(12) United States Patent
Leafloor et al.

(10) Patent No.: US 10,990,771 B2
(45) Date of Patent: Apr. 27, 2021

(54) SENSOR CABLE SETUP METHOD AND COMPUTER-READABLE MEDIUM FOR SETTING UP SENSOR CABLES IN GRAIN BIN

(71) Applicant: AG Growth International Inc., Winnipeg (CA)

(72) Inventors: Erron Leafloor, Winnipeg (CA); Craig Nimegeers, Winnipeg (CA)

(73) Assignee: AG GROWTH INTERNATIONAL INC., Winnipeg (CA)

( * ) Notice: Subject to any disclaimer, the term of this patent is extended or adjusted under 35 U.S.C. 154(b) by 128 days.

(21) Appl. No.: 16/166,793

(22) Filed: Oct. 22, 2018

(65) Prior Publication Data
US 2019/0122014 A1 Apr. 25, 2019

Related U.S. Application Data

(60) Provisional application No. 62/575,400, filed on Oct. 21, 2017.

(51) Int. Cl.
| | |
|---|---|
| *G06K 7/10* | (2006.01) |
| *G06K 7/14* | (2006.01) |
| *G01K 1/14* | (2021.01) |
| *G01K 15/00* | (2006.01) |
| *G01N 33/02* | (2006.01) |
| *G01K 13/10* | (2006.01) |

(52) U.S. Cl.
CPC ........... *G06K 7/10297* (2013.01); *G01K 1/14* (2013.01); *G01K 13/10* (2013.01); *G01K 15/005* (2013.01); *G01N 33/025* (2013.01); *G06K 7/1413* (2013.01)

(58) Field of Classification Search
CPC .. G06K 7/10297; G06K 7/1413; G01K 13/10; G01K 1/14; G01K 15/005; G01N 33/025
See application file for complete search history.

(56) References Cited

U.S. PATENT DOCUMENTS

| | | | | |
|---|---|---|---|---|
| 6,784,802 | B1 * | 8/2004 | Stanescu | H04Q 1/138 340/687 |
| 8,701,979 | B2 * | 4/2014 | Yokota | H02G 3/00 235/375 |
| 2014/0046611 | A1 * | 2/2014 | Bloemendaal | G01N 27/223 702/65 |
| 2015/0177114 | A1 * | 6/2015 | Kapoor | G01N 33/0098 702/128 |

(Continued)

FOREIGN PATENT DOCUMENTS

CA  2891018 A1 * 11/2016 ............. H04W 4/70

*Primary Examiner* — Sonji N Johnson
(74) *Attorney, Agent, or Firm* — Ware, Fressola, Maguire & Barber LLP

(57) ABSTRACT

A system for storing and monitoring grain includes a grain bin for storing grain and a plurality of sensor cables suspended within the grain bin, the sensor cables comprising sensors for sensing one or both of the temperature and humidity of the grain. The system further includes a mobile device for reading codes on each of the sensor cables, wherein the mobile device assigns a cable location inside the grain bin to each of the sensor cables. In a manual setup, the mobile device displays a representation of a cable configuration, displays a request to connect the sensor cables in indicated locations and then assigns the cable locations to each sensor cable.

21 Claims, 32 Drawing Sheets

(56) References Cited

U.S. PATENT DOCUMENTS

2016/0330270 A1* 11/2016 Folk .................. H04W 4/70
2017/0346953 A1* 11/2017 Abassi ............... H04M 11/007
2018/0356313 A1* 12/2018 Russell Jackson ... G01F 11/003

* cited by examiner

Step 1. Disconnect all cables.

Step 2. Connect cable.

Physically connect a cable and press "CONFIRM CONNECTION" for system to verify that it has been added.

Step 3. Confirm.

Yard: South yard

Bin: Westeel Centurion-W 1505

- Cable #1  ID: 74165456
- Nearest to the South Side  ID: 7416...
- Cable #3  ID: 74165497
- Cable #4  ID: 74165456
- Cable #5  ID: 74165488

CONFIRM    CANCEL

SENSOR CABLE SETUP METHOD AND COMPUTER-READABLE MEDIUM FOR SETTING UP SENSOR CABLES IN GRAIN BIN

CROSS-REFERENCE TO RELATED APPLICATIONS

This application claims benefit to provisional application Ser. No. 62/575,400, filed 21 Oct. 2017, which is incorporated by reference in their entirety.

TECHNICAL FIELD

The present invention relates generally to grain bins and more specifically to devices and methods for measuring temperature and moisture of grain being stored inside grain bins.

BACKGROUND

Grain bins are used to store grain. Measuring the moisture content (relative humidity) of the grain and temperature of the grain is important to know how long the grain can be stored and also to control any climate control devices used to regulate the temperature and/or humidity inside the grain bin.

Temperature and moisture sensor cables are widely used in the agricultural industry for monitoring grain conditions of grain stored inside a grain bin. The sensor cables, which are hung from the inside roof or ceiling of the grain bin, are communicatively connected to a data collection device or local monitoring device which transmits the data, for example wirelessly, to a remote monitoring station or device. Together the sensor cables, data collection device and monitoring device form a grain bin monitoring system. For large grain bins, the grain bin monitoring system requires multiple sensor cables to hang from the roof of the grain bin to obtain temperature and relative humidity values at different locations throughout the grain. These sensor cables are often disposed in a standard geometric pattern. To make the most use of the data, users often associate a given sensor cable with a given geometric position.

In order to indicate the position of the sensor cables, users typically need to either wire a specific sensor cable to a specific location on the data collection device that is reading the sensor cables, or manually indicate to the device which sensor cable is where through an indexing tool. These methods require that the installer climb onto the roof of the grain bin to perform the cable configuration task. Climbing onto the roof of a grain bin is time-consuming and inconvenient.

It would be desirable to simplify and improve the setup of the systems used for measuring temperature and moisture inside grain bins to address at least some of these issues.

SUMMARY

The following presents a simplified summary of some aspects or embodiments of the invention in order to provide a basic understanding of the invention. This summary is not an extensive overview of the invention. It is not intended to identify key or critical elements of the invention or to delineate the scope of the invention. Its sole purpose is to present some embodiments of the invention in a simplified form as a prelude to the more detailed description that is presented later.

Accordingly, one inventive aspect of the present disclosure is a method of automatically configuring sensor cables for measuring temperature and moisture inside a grain bin, the method comprising reading codes for a plurality of sensor cables within the grain bin using a mobile device and assigning cable locations within the grain bin to each of the sensor cables.

Another inventive aspect is a computer-readable medium comprising programmed instructions which when stored by a memory of a mobile device and executed by a processor of the mobile device cause the mobile device to read codes for a plurality of sensor cables within the grain bin using a mobile device and to assign cable locations within the grain bin to each of the sensor cables.

Another inventive aspect is a system for storing and monitoring grain, the system comprising a grain bin for storing grain and a plurality of sensor cables suspended within the grain bin. The sensor cables comprise sensors for sensing one or both of the temperature and humidity of the grain. The system includes a mobile device having a reader for reading codes on each of the sensor cables and for assigning cable locations to each of the sensor cables.

A further inventive aspect of the present disclosure is a method of manually configuring sensor cables for measuring temperature and moisture inside a grain bin, the method comprising displaying on a display of a mobile device a representation of a cable configuration, displaying a request to the user to connect the sensor cables in locations indicated on the cable configuration and assigning, using a processor of the mobile device, cable locations within the grain bin to each of the sensor cables in response to user input confirming that the cables have been connected. The mobile device may be configured to take a reading to verify that it is receiving all signals. Alternatively, the assigning may be done by a remote computing device such as a cloud-based server.

A further inventive aspect of the present disclosure is a computer-readable medium comprising programmed instructions which when stored by a memory of a mobile device and executed by a processor of the mobile device cause the mobile device to display on a display of a mobile device a representation of a cable configuration, display a request to the user to sequentially connect the sensor cables in locations sequentially indicated on the cable configuration and assign, using a processor of the mobile device, cable locations within the grain bin to each of the sensor cables in response to user input confirming that the cables have been connected. Alternatively, the assigning may be done by a remote computing device such as a cloud-based server.

A further inventive aspect of the present disclosure is a system for storing and monitoring grain, the system comprising a grain bin for storing grain and a plurality of sensor cables suspended within the grain bin, the sensor cables comprising sensors for sensing one or both of the temperature and humidity of the grain. The system also includes a mobile device configured to display on a display of the mobile device a representation of a cable configuration, display a request to the user to sequentially connect the sensor cables in locations sequentially indicated on the cable configuration and assign, using a processor of the mobile device, cable locations within the grain bin to each of the sensor cables in response to user input confirming that the cables have been connected. Alternatively, the assigning may be done by a remote computing device such as a cloud-based server.

BRIEF DESCRIPTION OF THE DRAWINGS

Further features and advantages of the present invention will become apparent from the following detailed description, taken in combination with the appended drawings in which.

It will be noted that throughout the appended drawings, like features are identified by like reference numerals.

DETAILED DESCRIPTION

Figure 1:
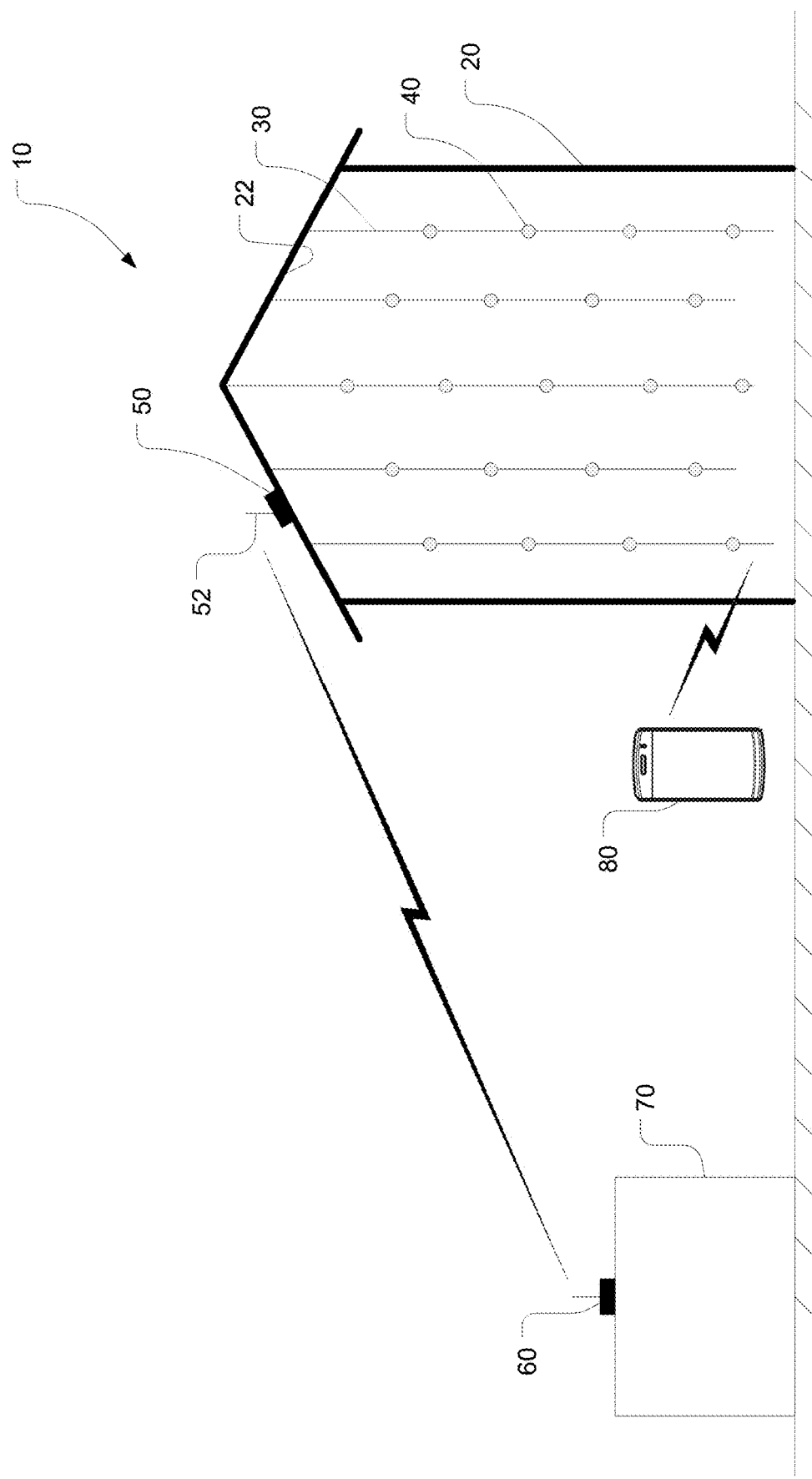
FIG. 1 depicts a system for storing and monitoring grain using sensors cables suspended inside a grain bin to measure temperature and moisture.

FIG. 1 depicts an exemplary system for storing and monitoring grain. The system is generally designated by reference numeral 10. The system 10 in the illustrated embodiment of FIG. 1 has a single grain bin 20 although it will be appreciated that the system may a plurality of grain bins. The grain bin shown in FIG. 1 has a generally cylindrical shape and a conical roof 22 although it will be appreciated that other shapes of grain bins may be employed. Beneath the conical roof (i.e. on the underside of the roof or ceiling of the roof) are suspended one or more sensor cables 30 for measuring the temperature and moisture (relative humidity) inside the grain bins. Each sensor cable 30 has one or more sensors. For example, the sensor cable 30 depicted in FIG. 1 has a plurality of sensors that are spaced apart along the length of the cable. The sensors may optionally be equally spaced apart as shown in the figure or, alternatively, the spacing may be unequal. The sensor cable 30 may have separate, alternating temperature and humidity sensors in one embodiment. In other embodiment, the sensor cable 30 may have integrated or packaged sensor nodes containing both a temperature and humidity sensor. The sensor cable may contain a communication wire and a power wire although in another embodiment, a single wire for both power and communication can be used. The temperature and humidity sensors transmit an analog or digital signal to a data collection device 50 mounted for example on the roof of the grain bin. The data collection device includes, or is connected to, a wireless transmitter 52 for transmitting the temperature and humidity data to a wireless receiver 60 at a remote monitoring station 70. The wireless transmitter 52 may be, for example, a cellular data transmitter, satellite transmitter, optical line-of-sight transmitter, Wi-Fi transmitter (for shorter distances) or any other suitable transceiver using any appropriate wireless transmission protocol. The remote monitoring station 70 may be, or may include, any suitable computing device, mobile device, cloud server, etc. The temperature and moisture data may be received remotely by a computing device (computer, laptop, wireless communications device, tablet, smart phone, etc) acting as the remote monitoring station using a wireless receiver or data receiver connected to a data network, e.g. the Internet. Alternatively, the data transmission may be over a wireline data connection. The cables can also be read by a handheld device that is carried from bin to bin.

In the case of a group of multiple grain bins, each grain bin may have its own wireless transmitter for transmitting temperature and moisture data obtained from the sensors cables for the particular grain bin. Alternatively, there may be a data aggregator to receive and aggregate data from each grain bin in a group of local bins and a single long-range (e.g. cellular) wireless transmitter for the group of bins.

Figure 2A:
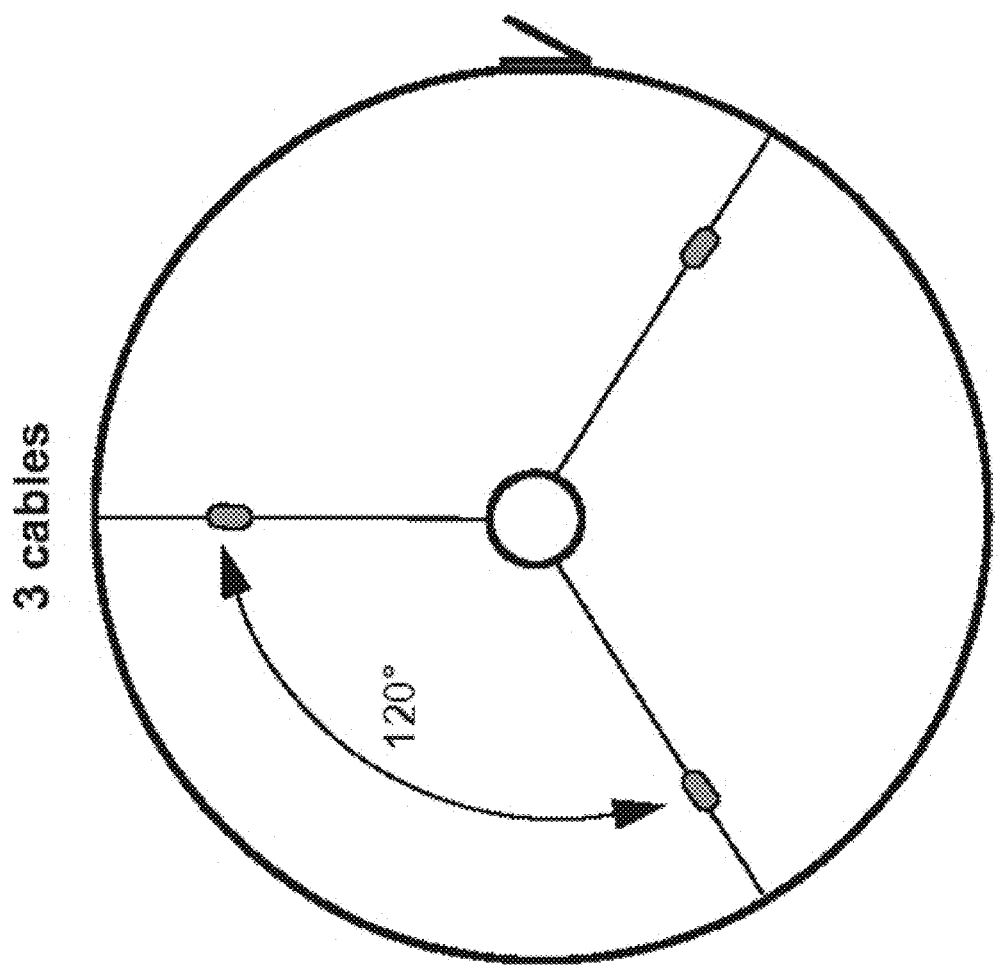
FIGS. 2A-2D depict various geometries of sensor cable configurations.
Figure 2A:
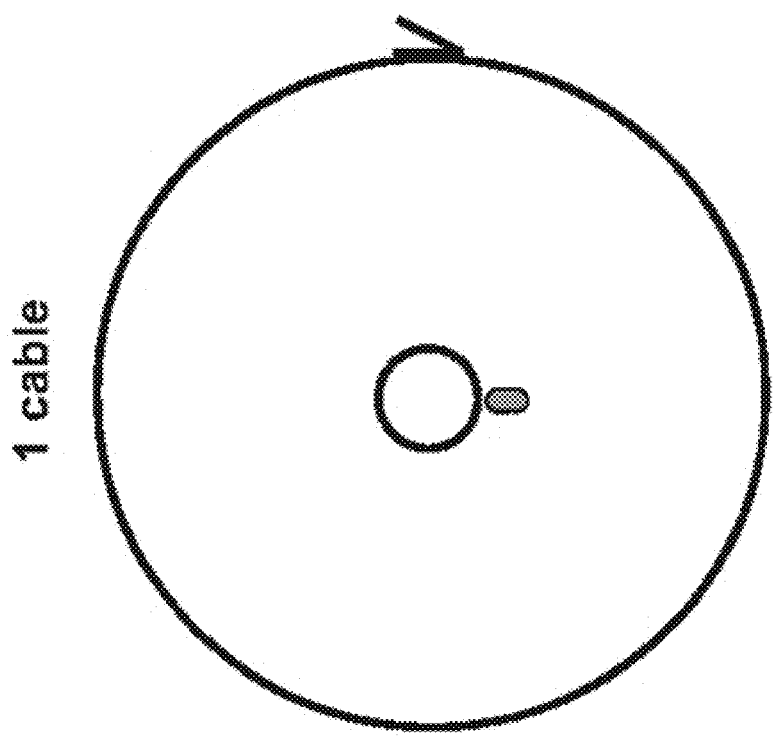
Figure 2B:
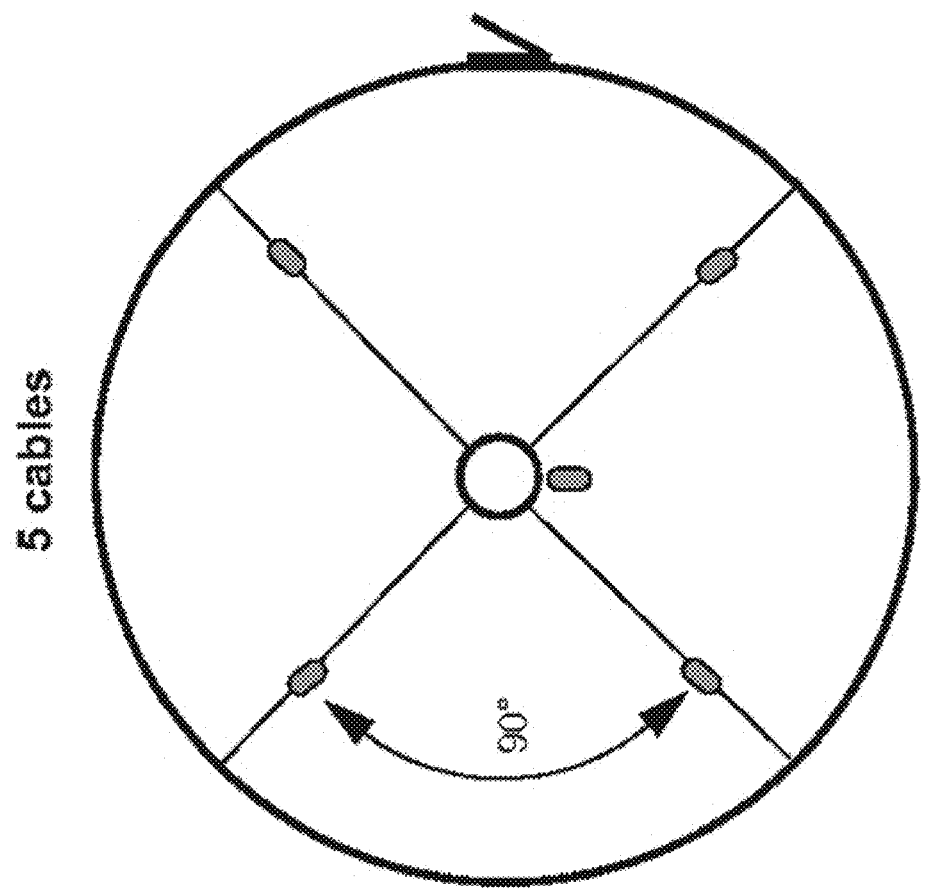
Figure 2B:
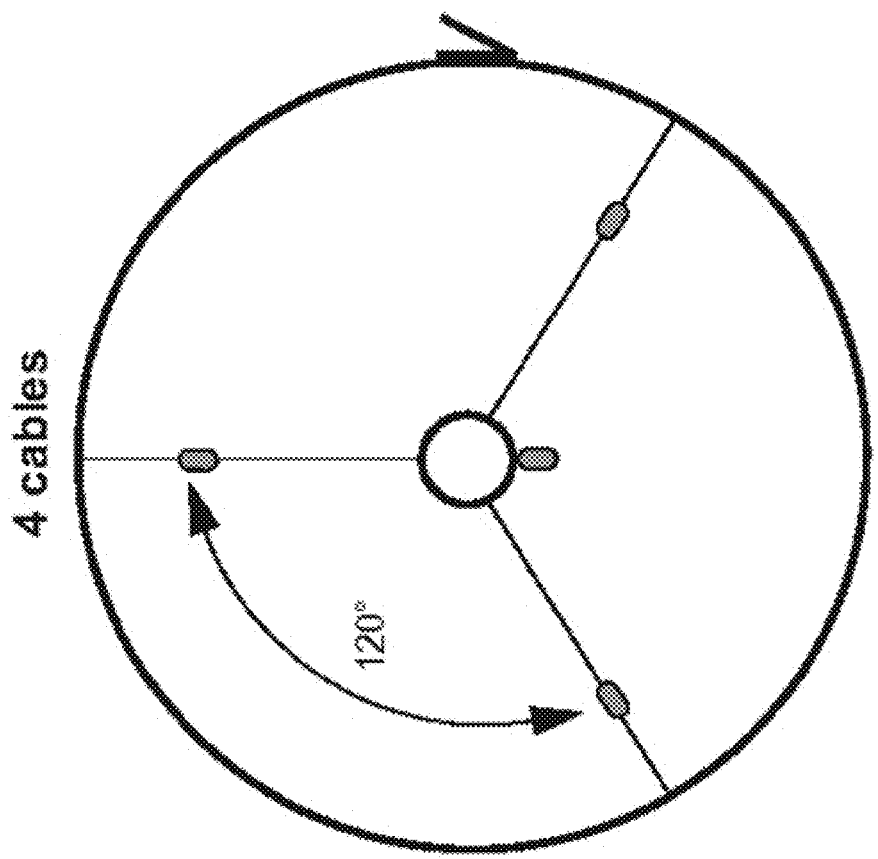
Figure 2C:
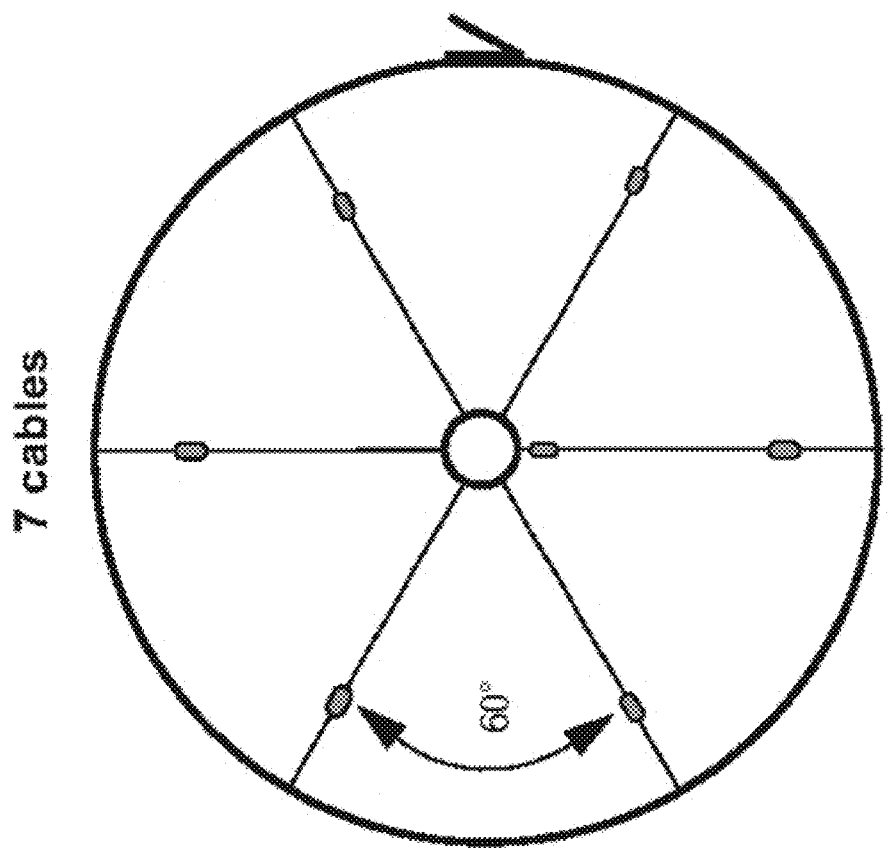
Figure 2C:
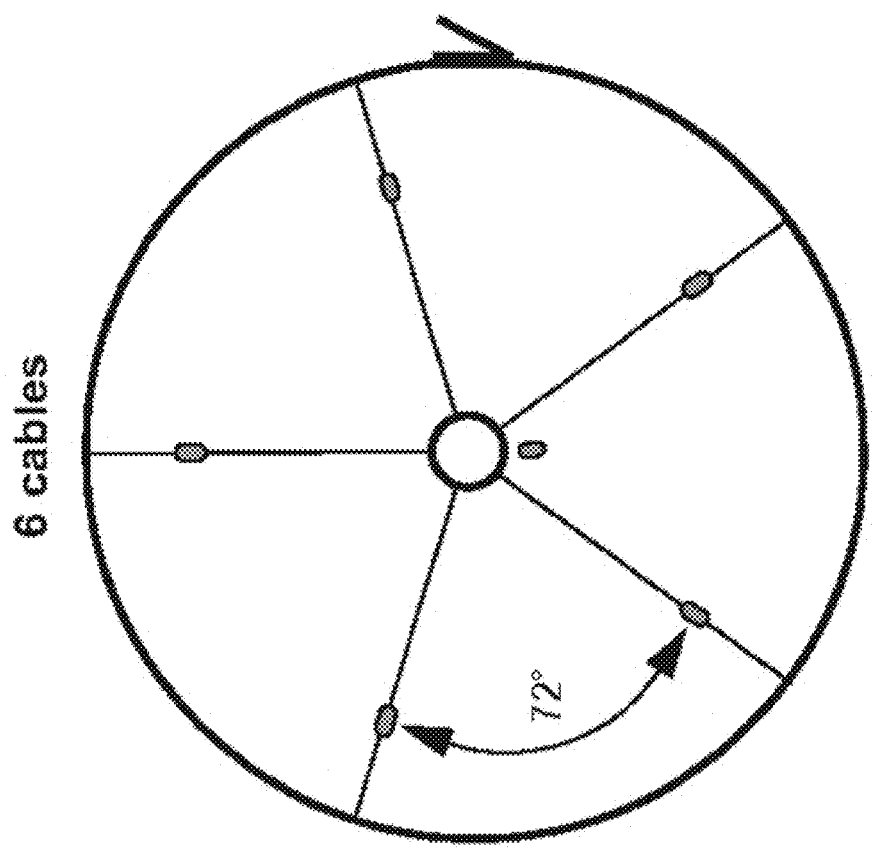
Figure 2D:
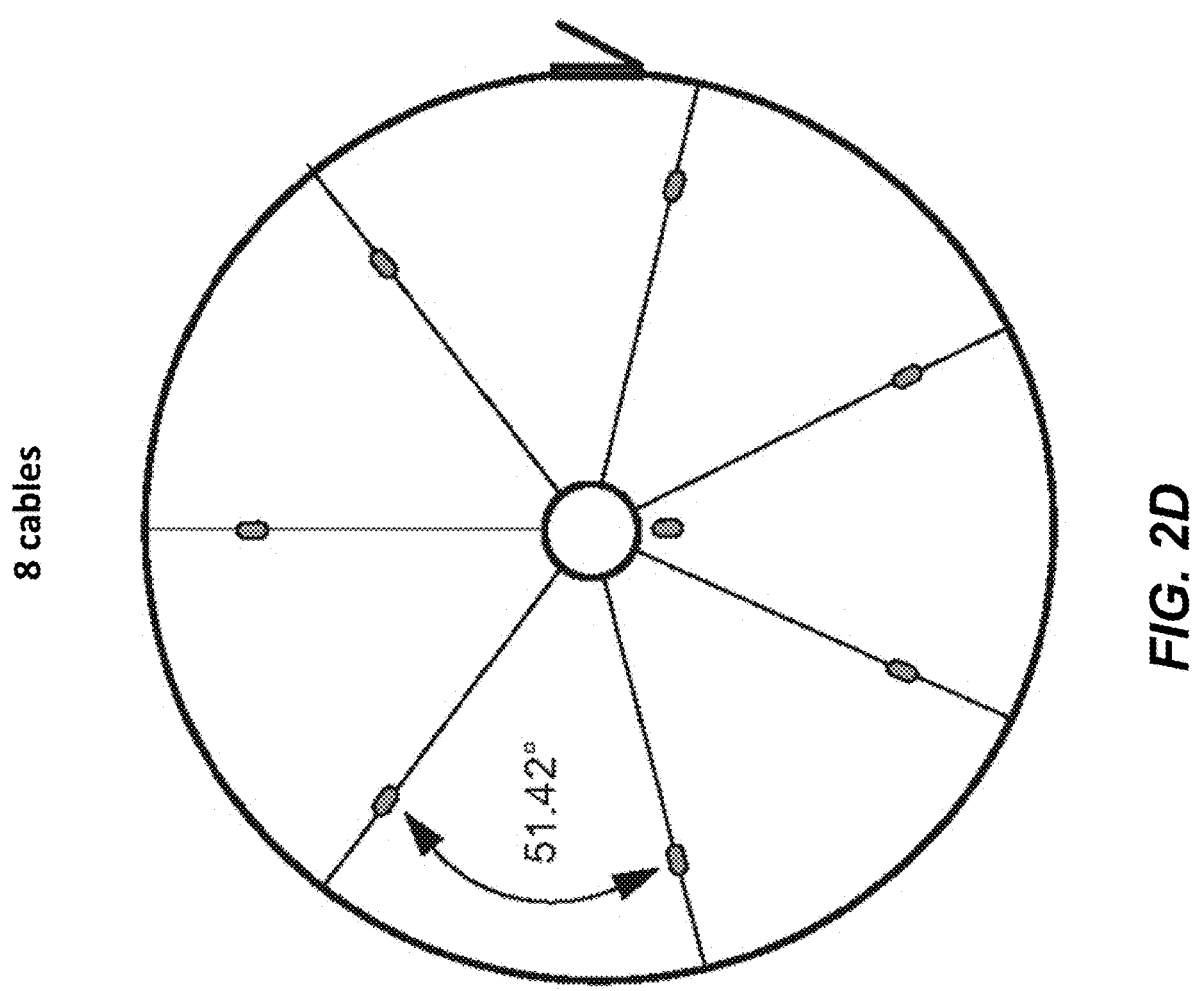

Although FIG. 1 shows that the grain bin has five sensor cables, any suitable number of sensor cables may be suspended in a given grain bin. The geometric configuration (cable configuration) may be varied depending on the size and geometry of the grain bin to be monitored. FIGS. 2A-2D depict some example cable configurations of sensor cables 30 for differently sized cylindrical bins. Specifically, FIG. 2A depicts 1-cable and 3-cable configurations. FIG. 2B depicts 4-cable and 5-cable configurations. FIG. 2C depicts 6-cable and 7-cable configurations. FIG. 2D depicts an 8-cable configuration.

In one embodiment, each sensor cable includes a structural cable having an upper end mounted to a roof (or ceiling) of the grain bin such that the structural cable is suspended inside the grain bin. In this embodiment, the structural cable has a central (longitudinal) cavity into which the sensor element cable is inserted. The temperature sensors in one embodiment are connected to a temperature sensor wire whereas the moisture sensors are connected to a moisture sensor wire. Each sensor cable in this embodiment has a control device that initiates the measurement and receives measurement data. The measurement devices can measure multiple cables at once, or a single cable. After the data is collected it is transmitted wirelessly, e.g. to a computing device such as a cloud server. Using an algorithm the relative humidity data is converted into grain moisture values. In the case of a cloud server implementation, a user can access the data on the cloud server through either a web interface or a mobile application.

As further depicted in FIG. 1, the system includes a mobile device 80 for use in setting up the sensor cables. The mobile device 80 may be a smart phone, cell phone, tablet, or any other wireless communications device or handheld mobile communication device. The mobile device includes a processor and a memory capable of storing computer-readable code that is executable by the processor to run a software application on the mobile device that enables a user or operator to set up the sensor cables by identifying which cable is located in which position. Knowing the disposition of each one of the sensor cables within the grain bin is useful in order to provide a more accurate representation or three-dimensional portrayal of the temperature and humidity profile of the grain in the grain bin. As described above, the conventional technique to set up sensor cables requires the user to climb atop the grain bin to configure the sensor cables which many consider to be time-consuming and inconvenient.

Embodiments of the present invention provide a novel and inventive method, system and computer-readable medium to greatly facilitate the task of configuring sensor cables for grain bins. The technique described herein decouples the configuration of the sensor cables from the installation of the sensor cables and brings the task down to ground level for convenience. A computer-readable medium such as a software application executing on a mobile device such as a smart phone indicates which cable is located where within the grain bin. In at least some embodiments, the mobile device remotely uploads the configuration data to a cloud server and then the cloud server sends the configuration data to the bin monitoring device (data collection device) on the roof of the bin. In at least some embodiments, the mobile device has a code reader to read a code, e.g. an optical code or an RF code. For example, the mobile device may use QR code scanning (or, alternatively, bar code scanning or any equivalent technology) to identify each of the cables without having to climb up onto the grain bin. For the purposes of this specification, the expression "optically scannable codes" are meant to encompass QR codes, bar codes or any equivalent code that may be scanned using a camera or optical scanner.

Although scannable optical codes, e.g. QR codes, are believed to be the best way to implement the present invention, other embodiments of the present invention may implement non-optical means such as, for example, radiofrequency identification (RFID) tags or near-field communication (NFC) chips. In these other non-optical embodiments, the mobile device is equipped with an RFID reader or NFC reader that is capable of reading the RFID tag or NFC chip installed in the sensor cable. Once the RFID tag or NFC chip has been read, the mobile device can process and/or transmit the data for processing, i.e. cable location assignment. It will be appreciated that any other suitable close proximity wireless transfer technology can be used, e.g. TransferJet.

In these non-optical embodiments, the method of automatically configuring sensor cables for measuring temperature and moisture inside a grain bin entails reading codes for a plurality of sensor cables within the grain bin using a mobile device and assigning cable locations within the grain bin to each of the sensor cables. The computer-readable medium comprises programmed instructions which when stored by a memory of a mobile device and executed by a processor of the mobile device cause the mobile device to read codes for a plurality of sensor cables within the grain bin using a mobile device and assign cable locations within the grain bin to each of the sensor cables. The system comprises a grain bin for storing grain, a plurality of sensor cables suspended within the grain bin, the sensor cables comprising sensors for sensing one or both of the temperature and humidity of the grain and a mobile device having a reader for reading codes on each of the sensor cables. In these non-optical embodiments, the reader is an RFID reader or NFC reader or equivalent reader. The mobile device is configured to wireless transmit the data read from the sensor cables via a wireless data connection to a cloud-based server for assignment of the cable locations.

The novel technique disclosed in this specification provides benefits in terms of convenience. The configuration data in some embodiments is transmitted to a cloud-based server or server cluster for access by the user or operator. Cloud storage enables access to the data even if the user has lost or misplaced his mobile device or if the mobile device is out of battery, without network access or otherwise inoperable. Cloud-based storage also allows the use of multiple devices to access this cable configuration data. In some embodiments, the data is also stored in a non-volatile memory of the mobile device.

Assigning the cable locations may be done locally by the mobile device or alternatively by a remote computing device such as a cloud-based server that is in communication via a data network with the mobile device.

Two techniques are described with reference to the drawings, a manual cable setup method, which is depicted in FIGS. 3-14, and an automatic (scanning-based) cable setup method, which is depicted in FIGS. 15-25. Improved manual and automatic methods are depicted in FIGS. 26A-26B and FIGS. 27A-27B.

The manual cable setup can be used for setting up ("onboarding") a bin that already has cables attached as well as for a new installation of cables having no code, e.g. no QR code or bar code. The automatic (scanning-based) cable setup can be used for cables having QR or bar codes that can be scanned. The QR code or bar code may be on or near the end of the cable close to the floor of the grain bin and thus easily accessible by a user who is inside the empty grain bin. It will be recalled that non-optical codes may also be utilized. It will be also be appreciated that in at least some embodiments, the codes are unique codes.

Figure 3:
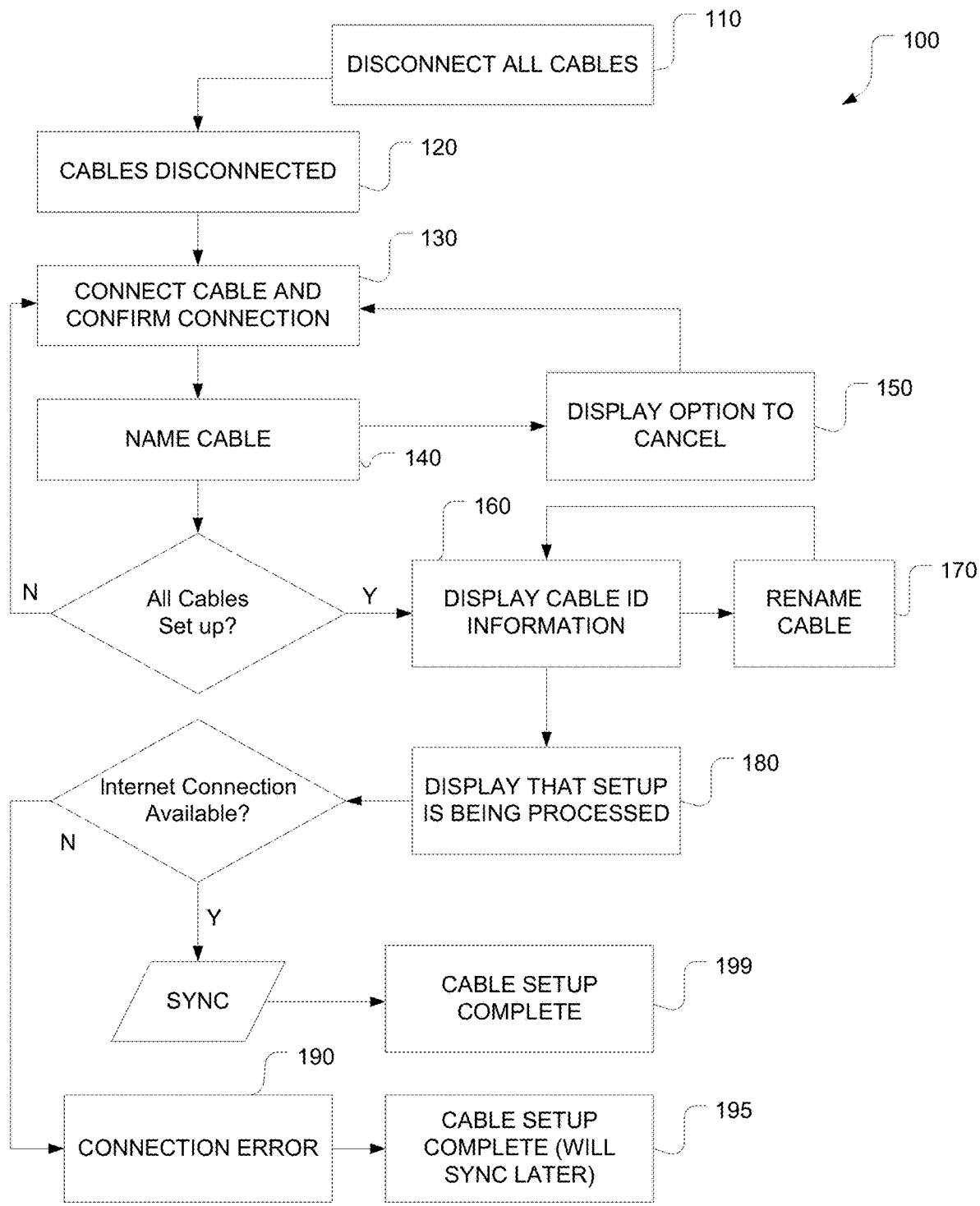
FIG. 3 is a flowchart of a method of manually setting up the sensor cables.

An overview of the manual cable setup technique is depicted in the flowchart of FIG. 3. The method 100 depicted by FIG. 3 entails steps of sequentially presenting various user interfaces via a display screen of a mobile device. As such, the application executing on the mobile device acts like a step-by-step guide or wizard to lead the user through the various steps of configuring the sensor cables. In other embodiments, the mobile device may audibly speak some or all of the instructions to the user in lieu of visually presenting information on the display screen of the mobile device.

Figure 4:
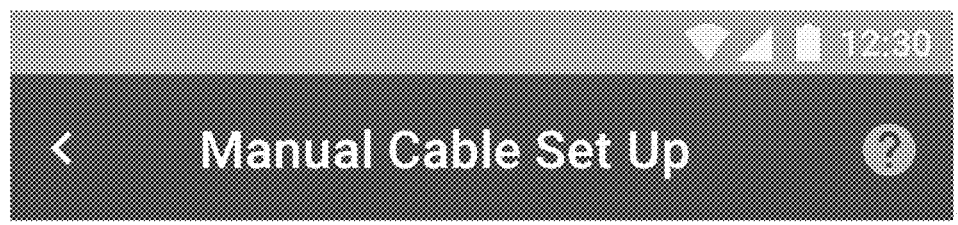
FIG. 4 depicts a graphical user interface displayed on a mobile device as part of the method of FIG. 3.
Figure 4:
Figure 4:
Figure 4:
Figure 5:
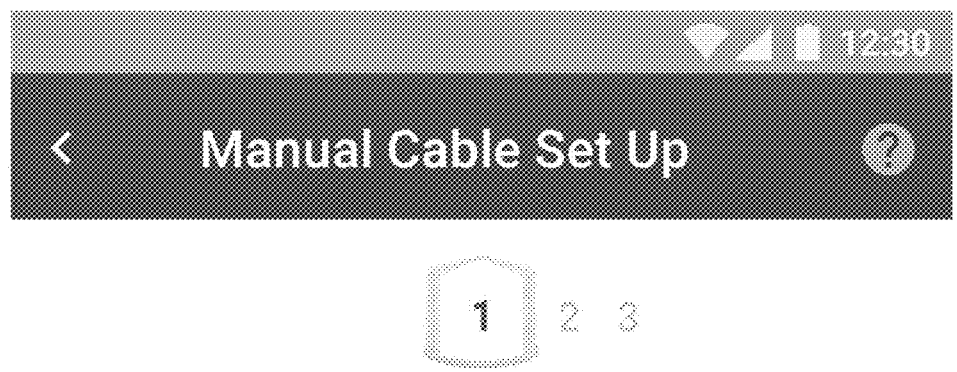
FIG. 5 depicts a graphical user interface displayed on a mobile device as part of the method of FIG. 3.
Figure 5:
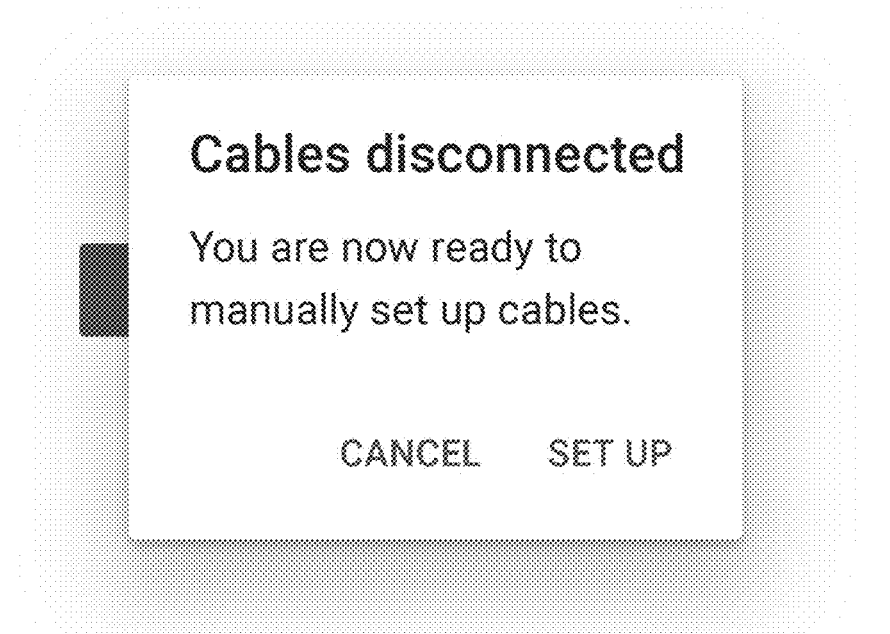
Figure 5:
Figure 6:
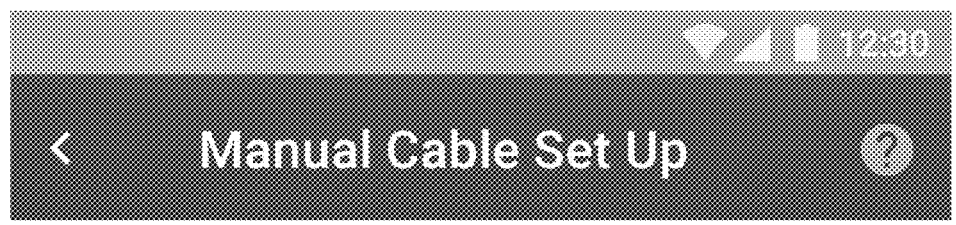
FIG. 6 depicts a graphical user interface displayed on a mobile device as part of the method of FIG. 3.
Figure 6:
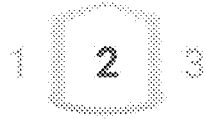
Figure 6:
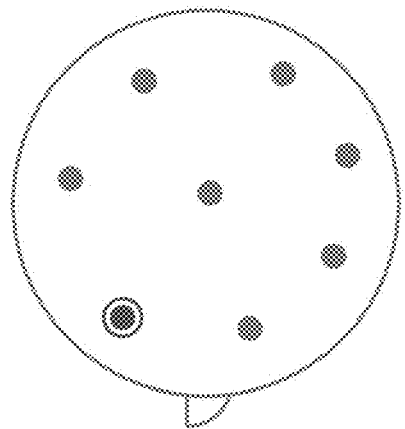
Figure 6:
Figure 7:
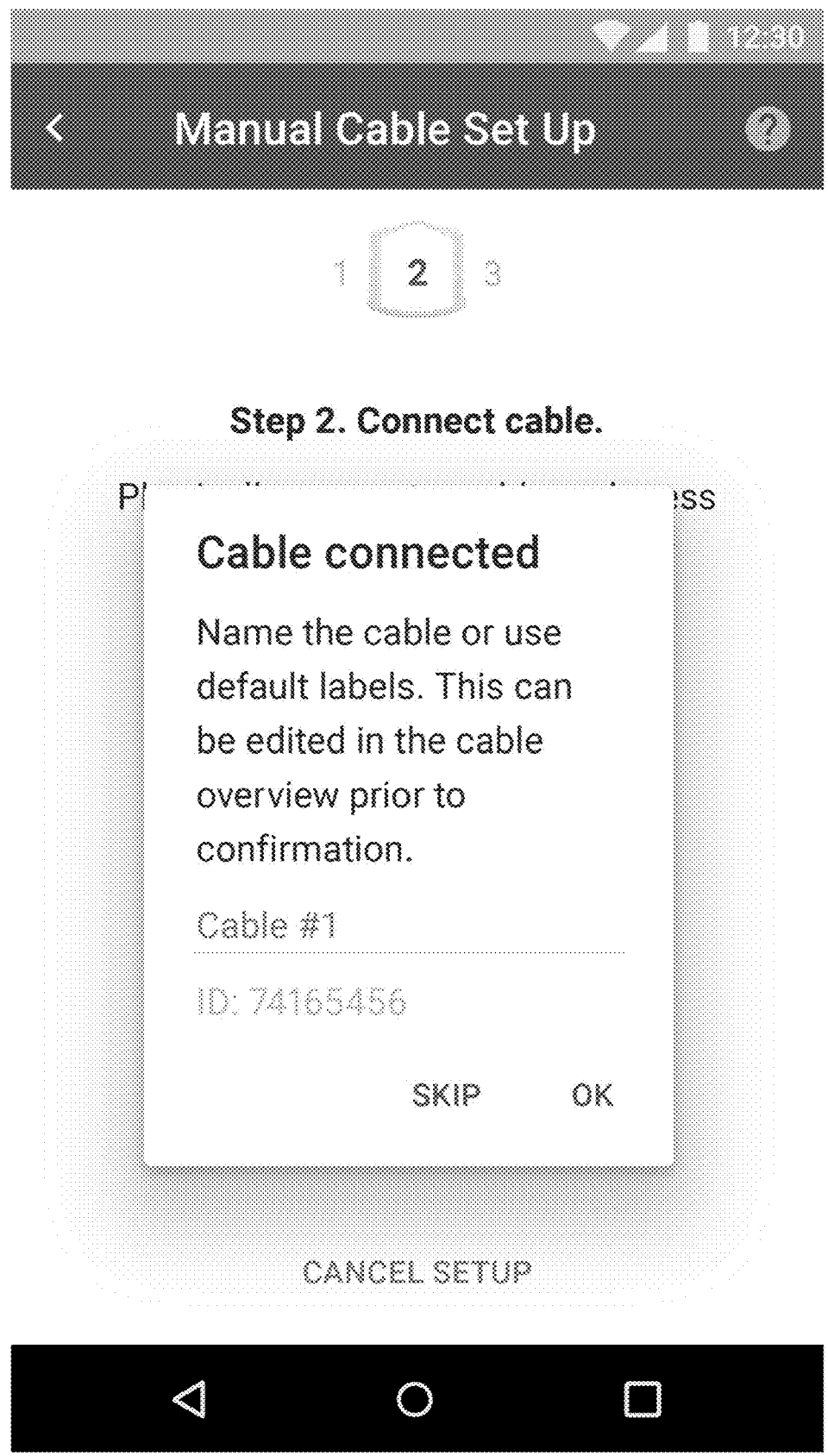
FIG. 7 depicts a graphical user interface displayed on a mobile device as part of the method of FIG. 3.
Figure 8:
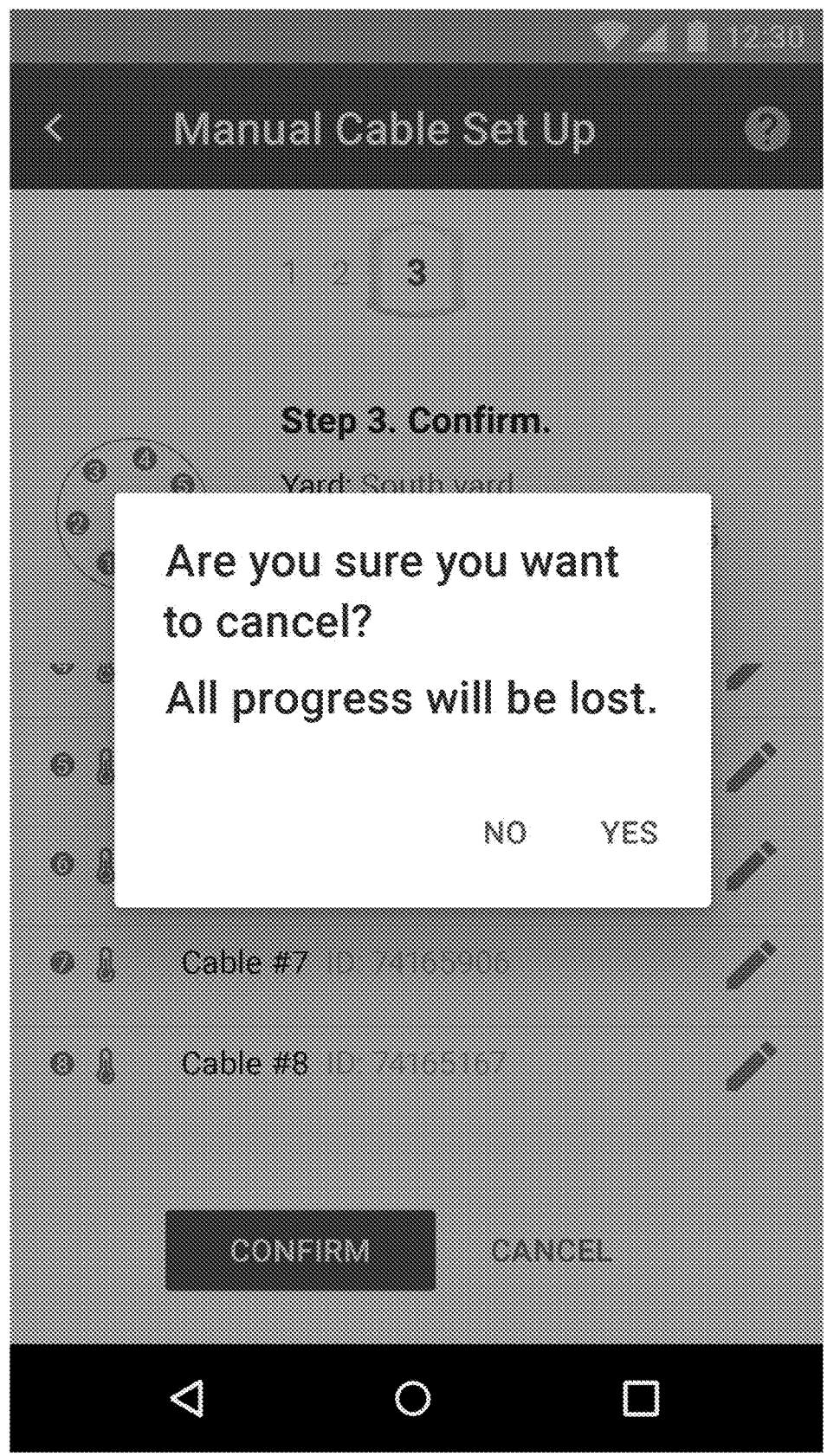
FIG. 8 depicts a graphical user interface displayed on a mobile device as part of the method of FIG. 3.
Figure 9:
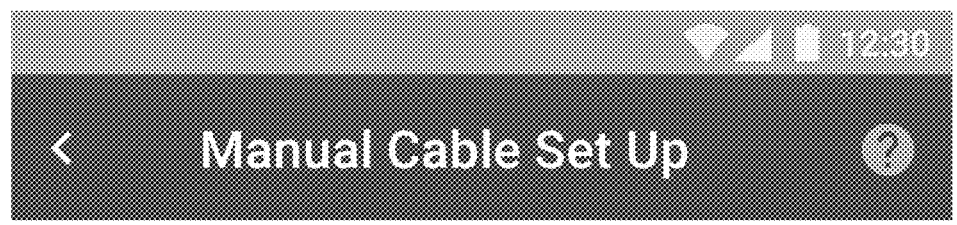
FIG. 9 depicts a graphical user interface displayed on a mobile device as part of the method of FIG. 3.
Figure 9:
Figure 9:
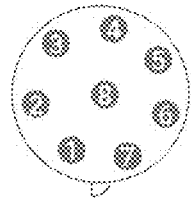
Figure 9:
Figure 10:
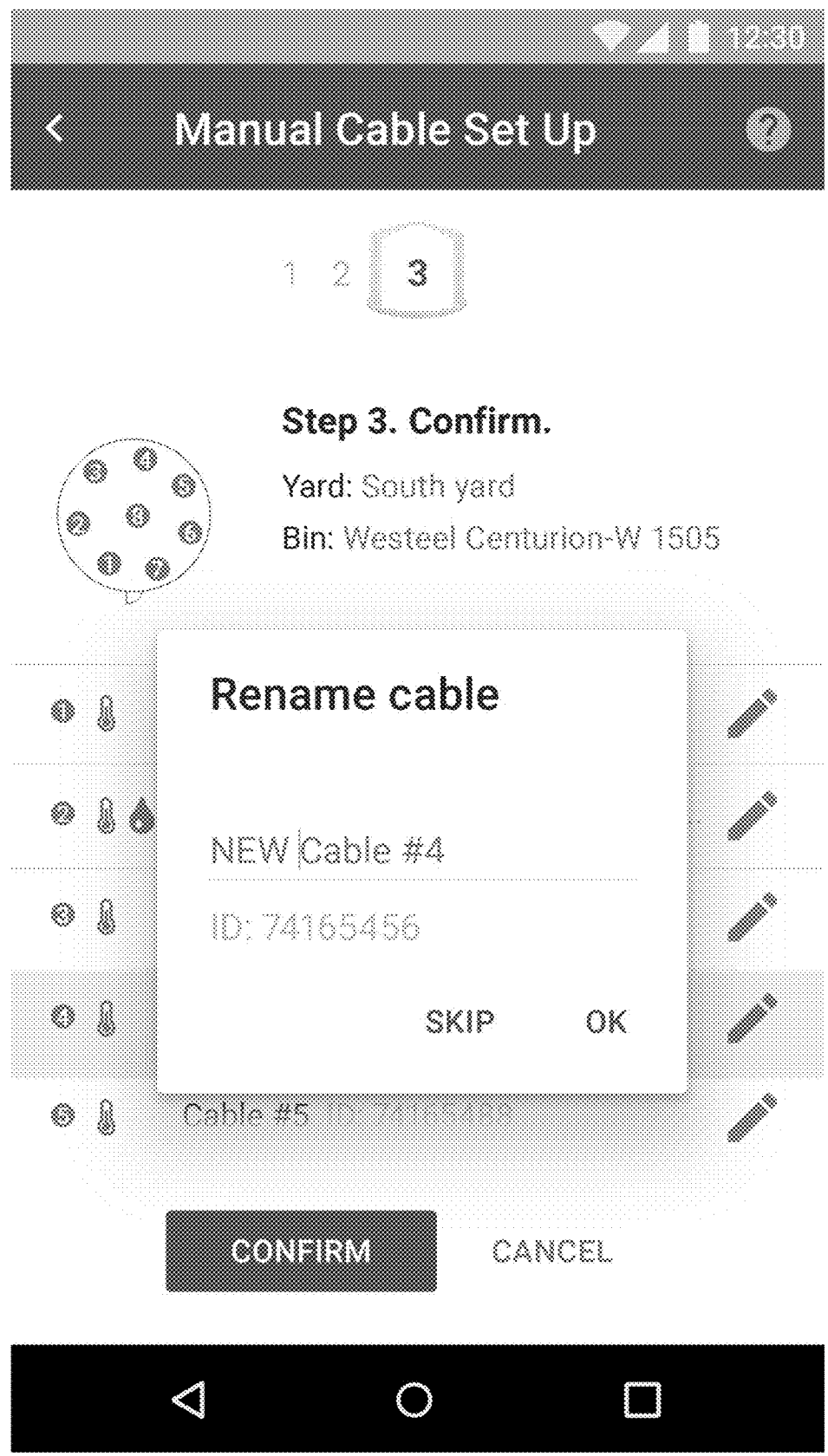
FIG. 10 depicts a graphical user interface displayed on a mobile device as part of the method of FIG. 3.
Figure 11:
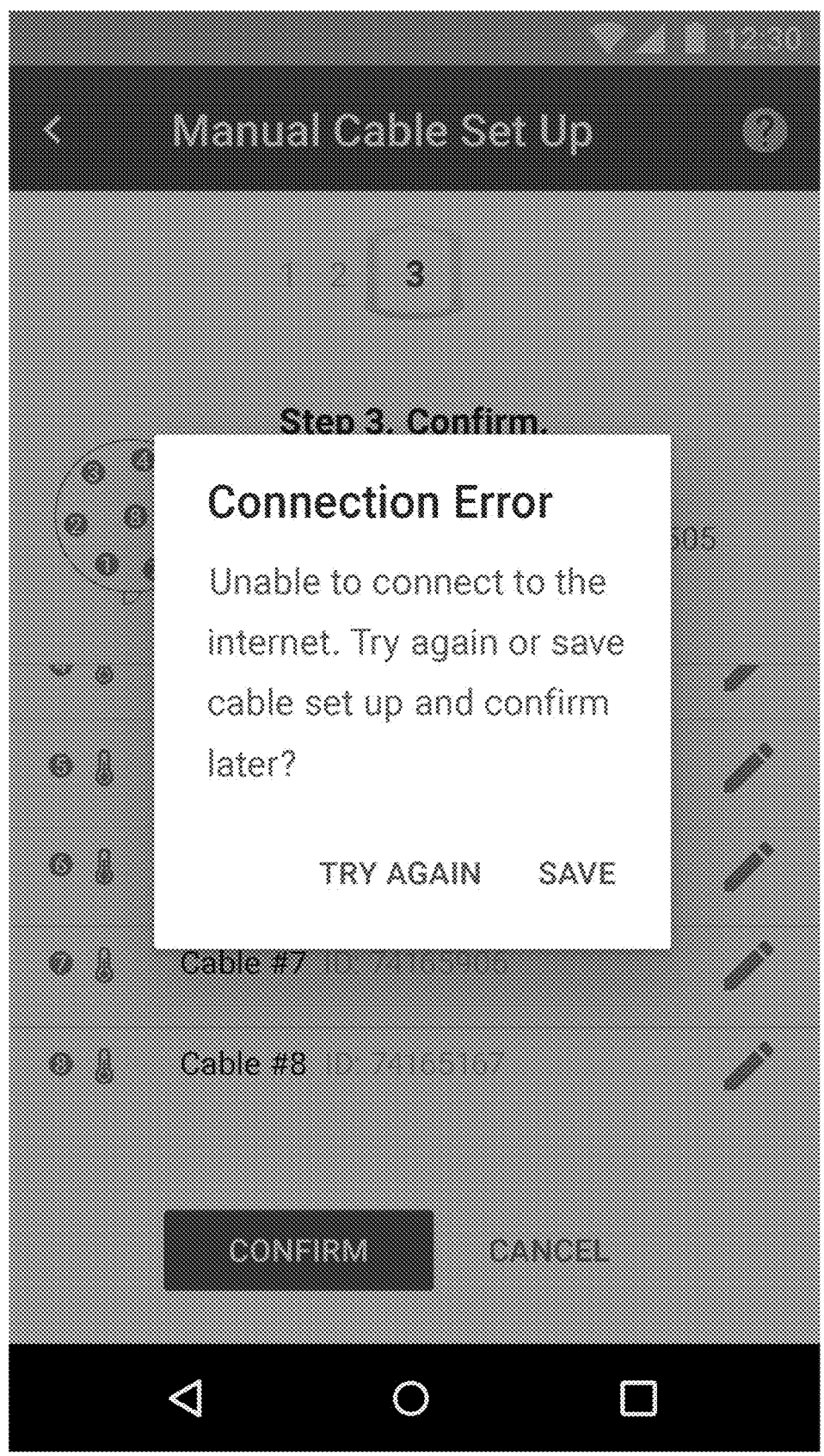
FIG. 11 depicts a graphical user interface displayed on a mobile device as part of the method of FIG. 3.
Figure 12:
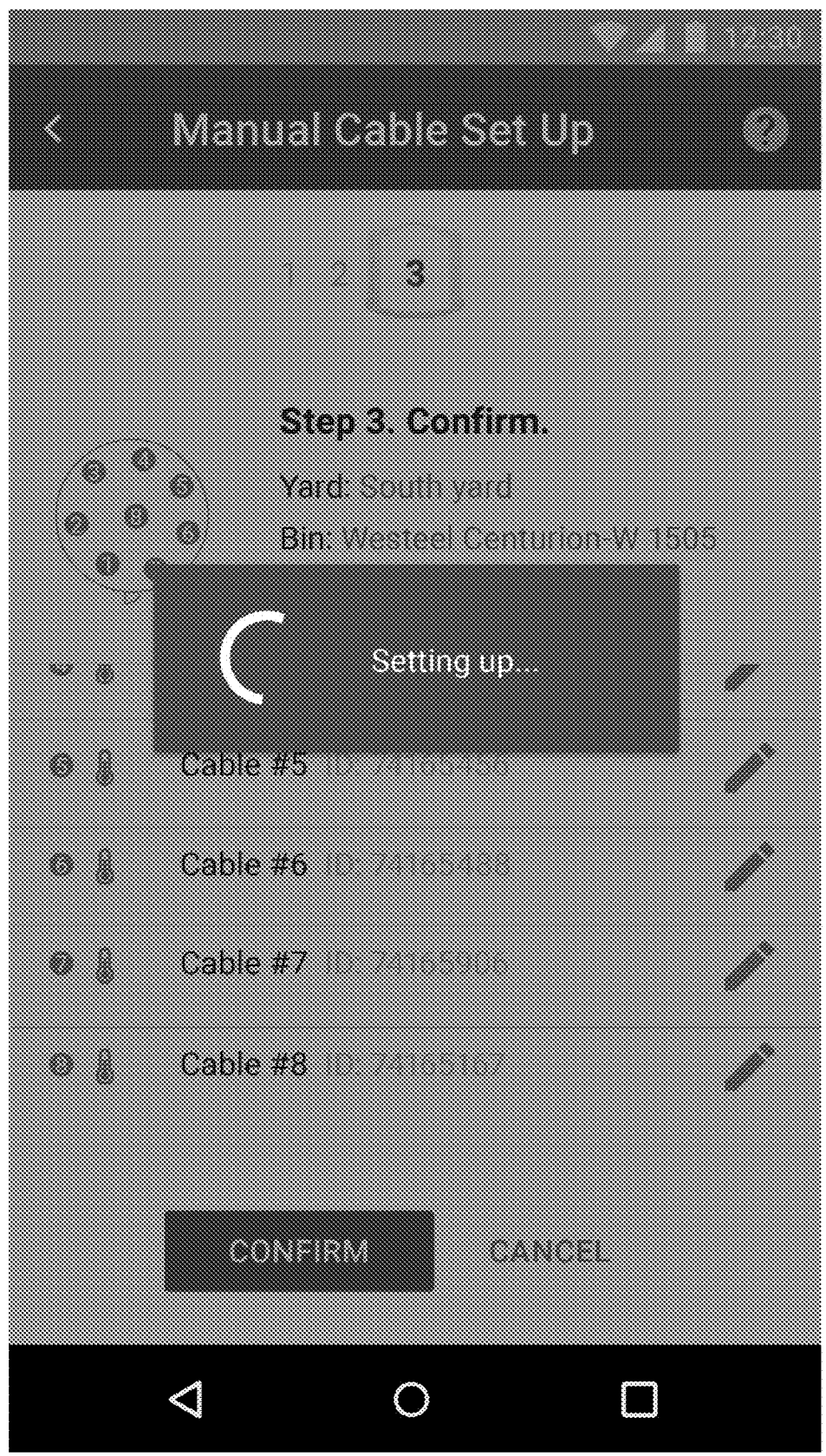
FIG. 12 depicts a graphical user interface displayed on a mobile device as part of the method of FIG. 3.
Figure 13:
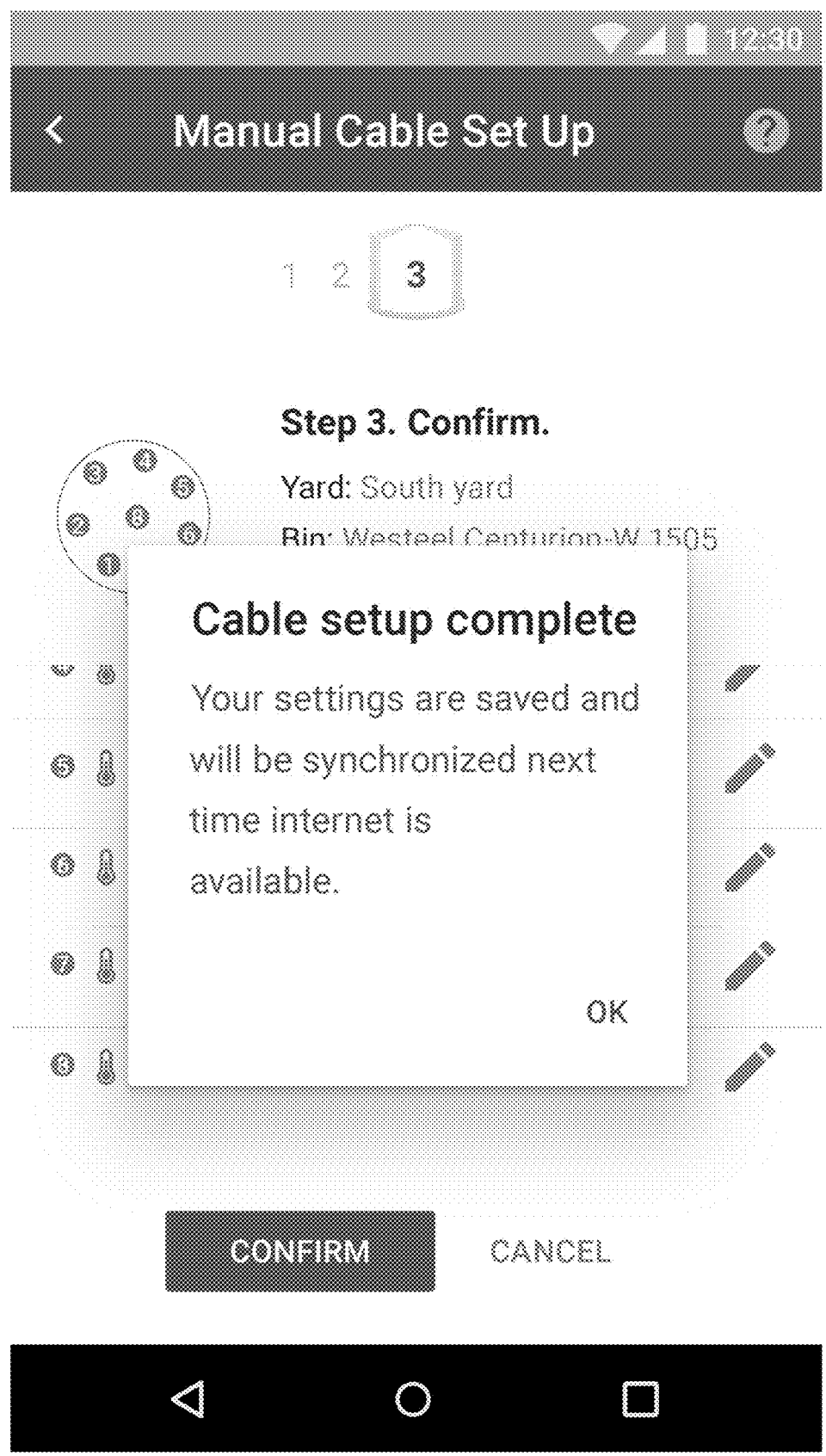
FIG. 13 depicts a graphical user interface displayed on a mobile device as part of the method of FIG. 3.
Figure 14:
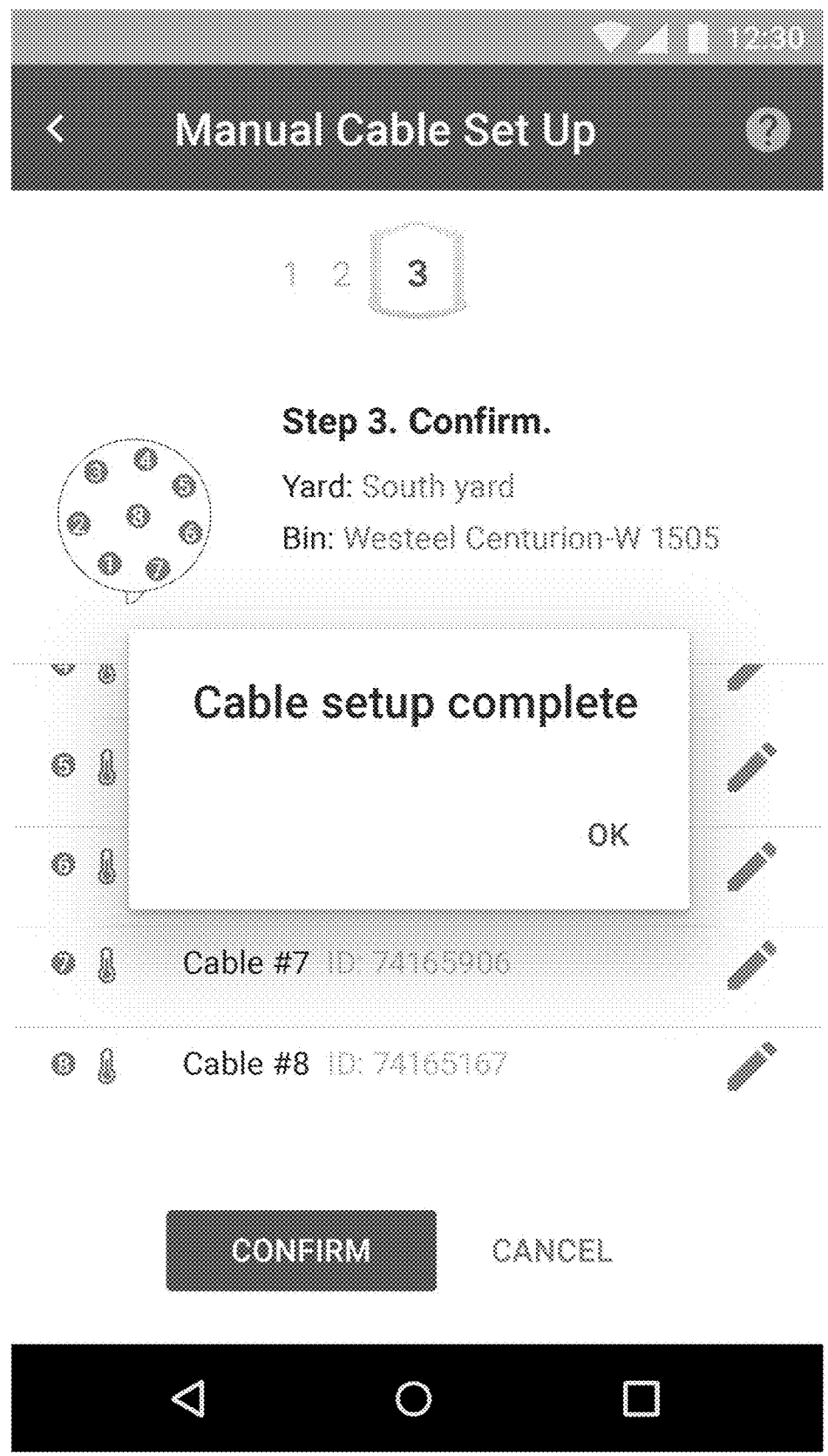
FIG. 14 depicts a graphical user interface displayed on a mobile device as part of the method of FIG. 3.

As shown by way of example in FIG. 3, the method 100 of manually setting up the sensor cables entails an initial step of displaying an initial setup screen and then subsequently presenting a message or notification to the user to disconnect all cables (step 110). An exemplary user interface (UI) that the mobile device can present onscreen to provide this message or notification is depicted in FIG. 4. A next step in the method is the display of a message that either one or more cables are still connected or that all cables have been disconnected (step 120) as the case may be. An exemplary user interface that the mobile device can present to provide this indication is depicted in FIG. 5. The app on the device may then say which cable to connect next. The app may also enable the user to skip to the next cable by presenting a suitable display on the UI. At step 130 of the method, the mobile device displays a request to the user to physically connect a cable and to confirm that the cable has been physically connected. An exemplary user interface for this step is depicted in FIG. 6. The mobile device then asks the user to name the cable or to use a default name or alphanumeric identifier at step 140. An exemplary user interface for this step is depicted in FIG. 7. An option to cancel is provided at step 150 using for example the user interface of FIG. 8. If this option is exercised, the app exits or restarts. At step 160, the mobile device displays cable identification information, e.g. using the user interface of FIG. 9. At step 170, the mobile device presents an option to rename a cable. FIG. 10 depicts an example user interface for this step. At step 180, and as shown by way of example in FIG. 12, the mobile device presents an indication that setup is being processed. If no internet connection is available, a connection error message is displayed at step 190 using a user interface such as the one shown in FIG. 11. The data is stored i.e. buffered until it can be later transmitted when the internet connection is available again. The mobile device may present a message that the data will be later synchronized (step 195) by displaying a message such as the one shown by way of example in FIG. 13. If an internet connection is available, the data is transmitted/synchronized and the mobile device presents an indication that the cable setup is now complete (step 199) by presenting for example a user interface such as the one shown in FIG. 14.

Figure 15:
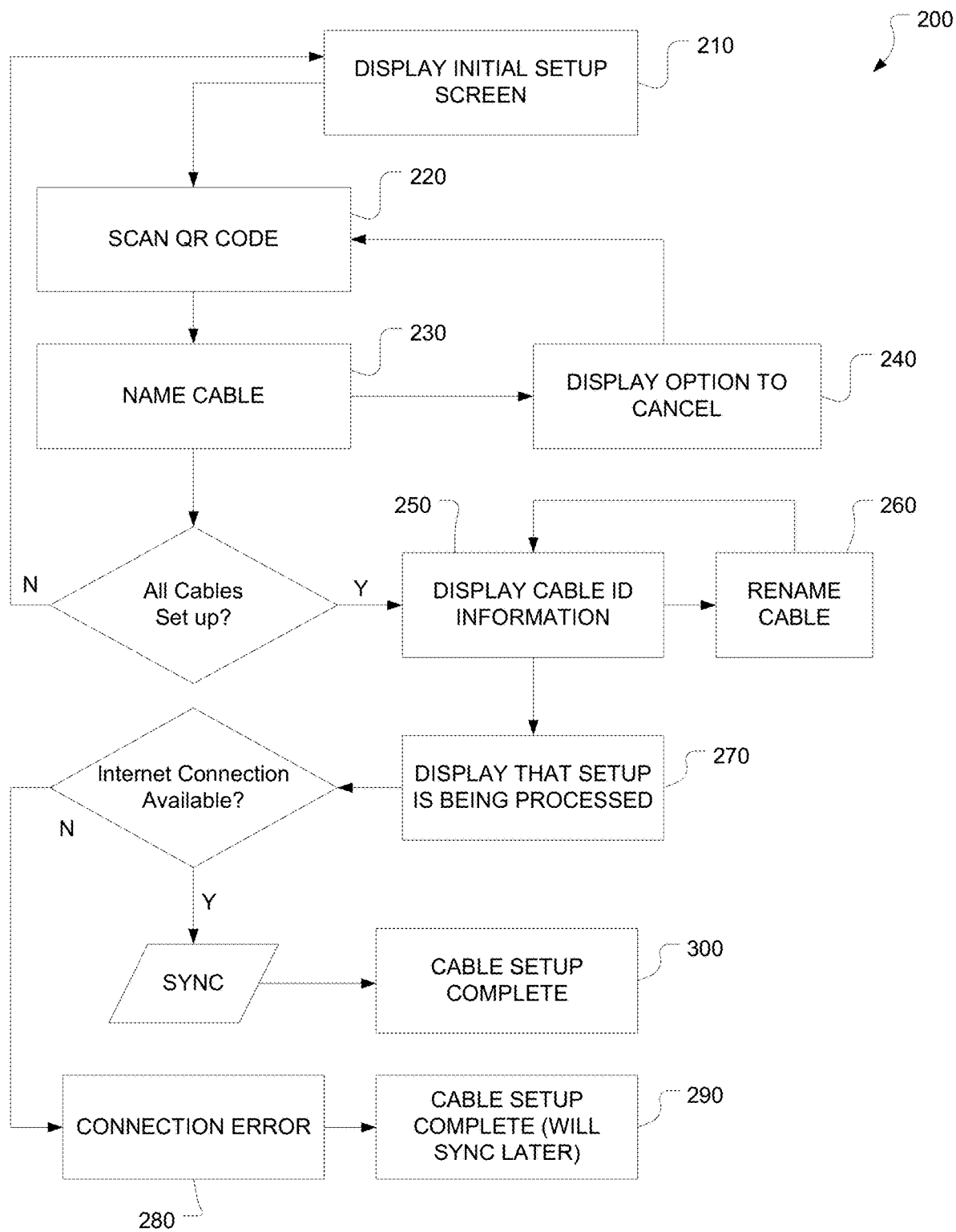
FIG. 15 is a flowchart of another (semi-automated) method of setting up the sensor cables.
Figure 16:
FIG. 16 depicts a graphical user interface displayed on a mobile device as part of the method of FIG. 15.
Figure 16:
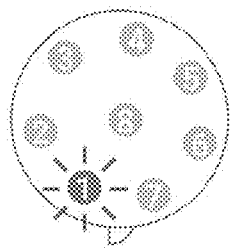
Figure 16:
Figure 16:
Figure 16:
Figure 17:
FIG. 17 depicts a graphical user interface displayed on a mobile device as part of the method of FIG. 15.
Figure 17:
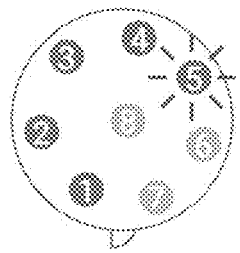
Figure 17:
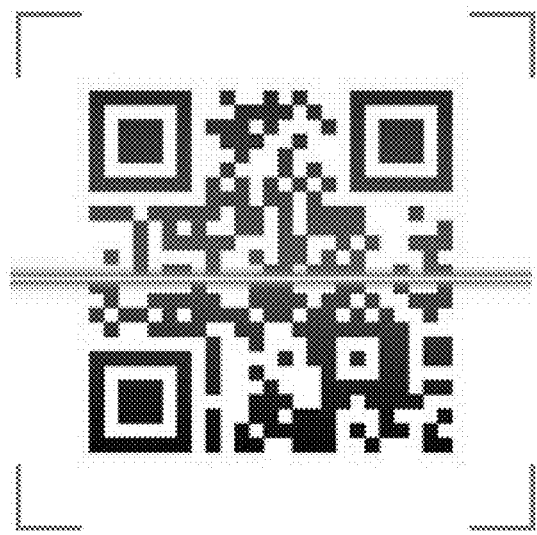
Figure 17:
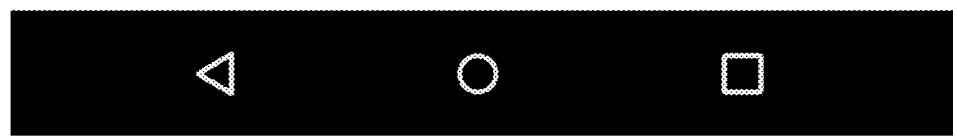
Figure 18:
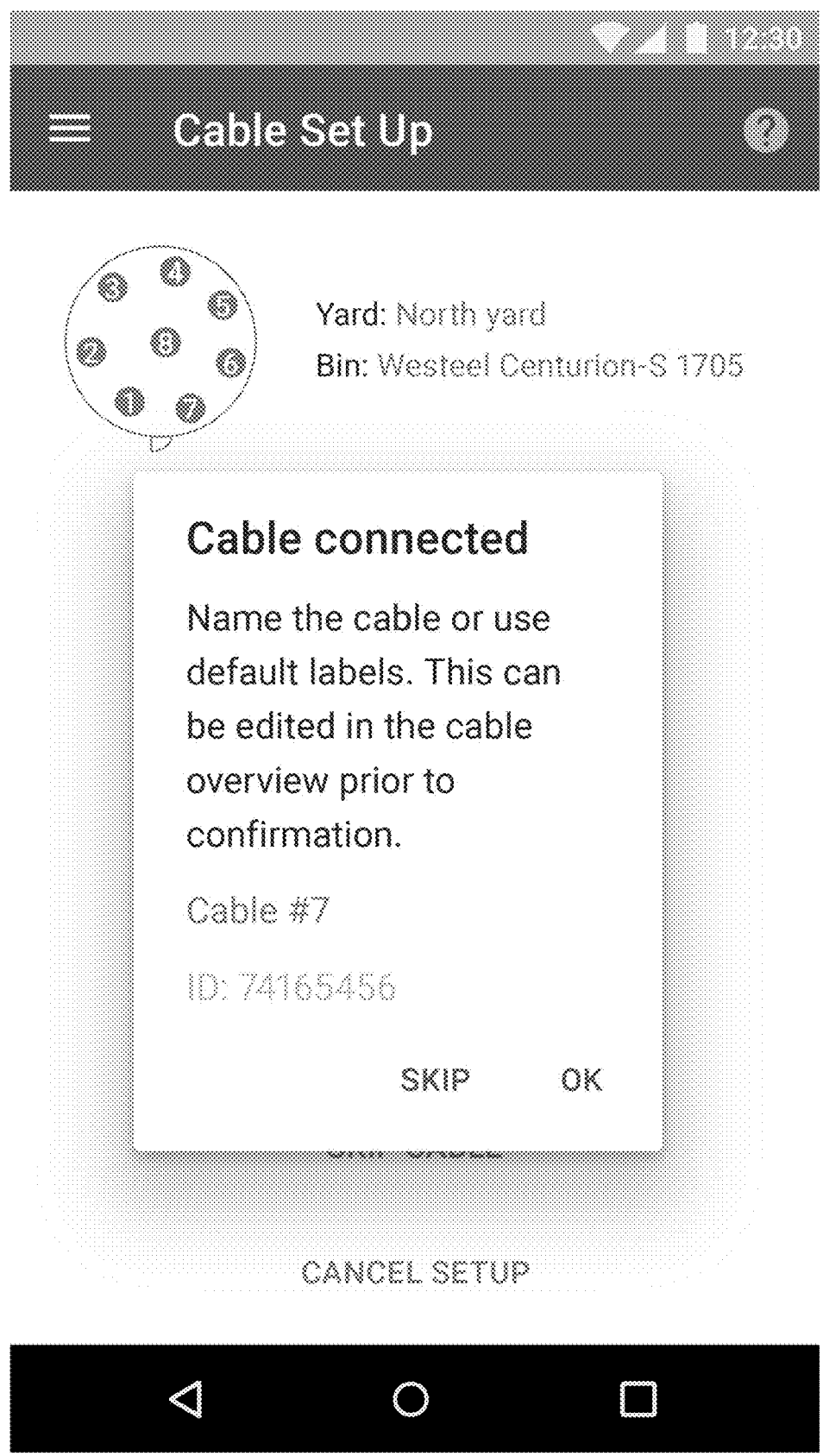
FIG. 18 depicts a graphical user interface displayed on a mobile device as part of the method of FIG. 15.
Figure 19:
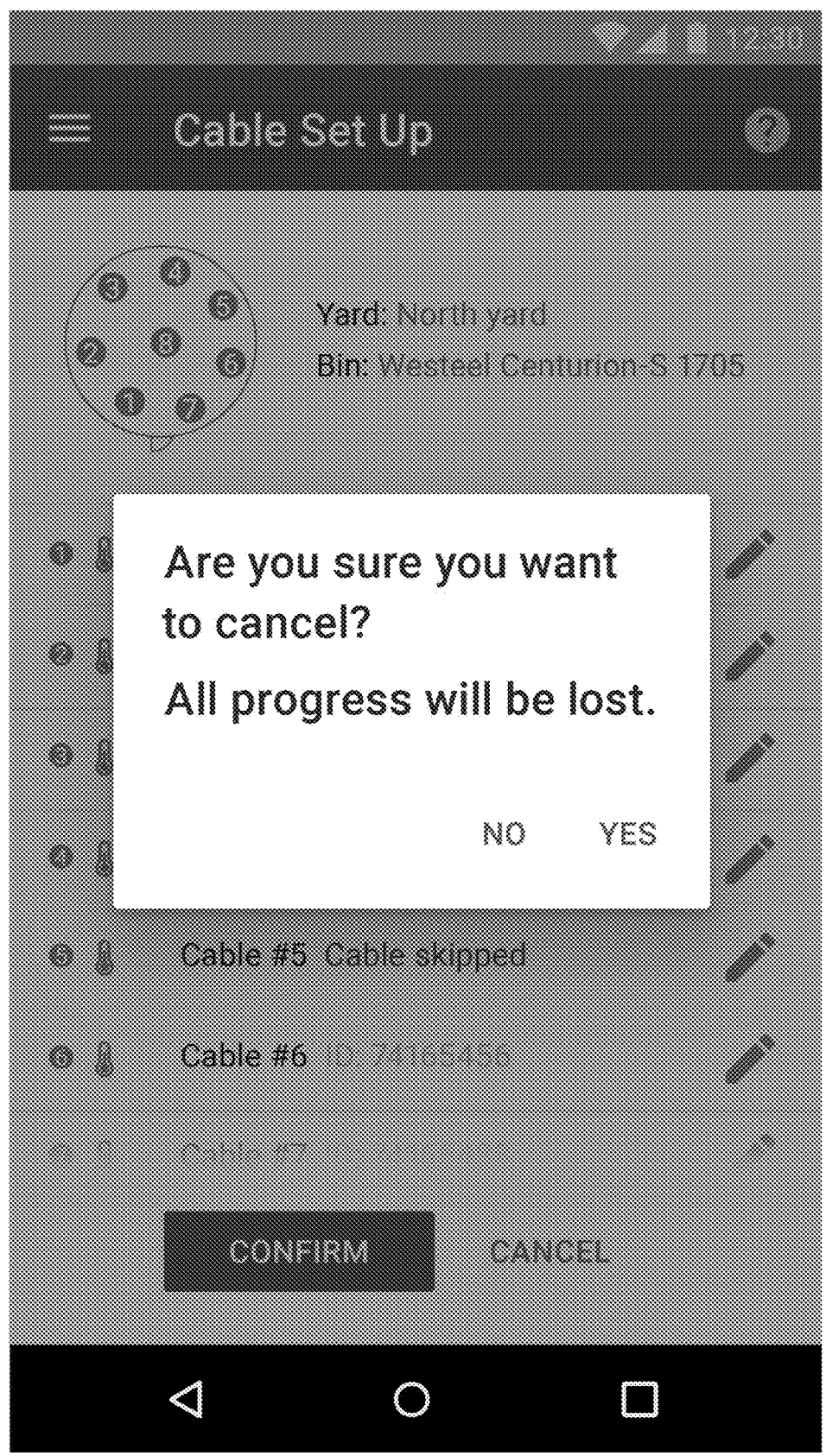
FIG. 19 depicts a graphical user interface displayed on a mobile device as part of the method of FIG. 15.
Figure 20:
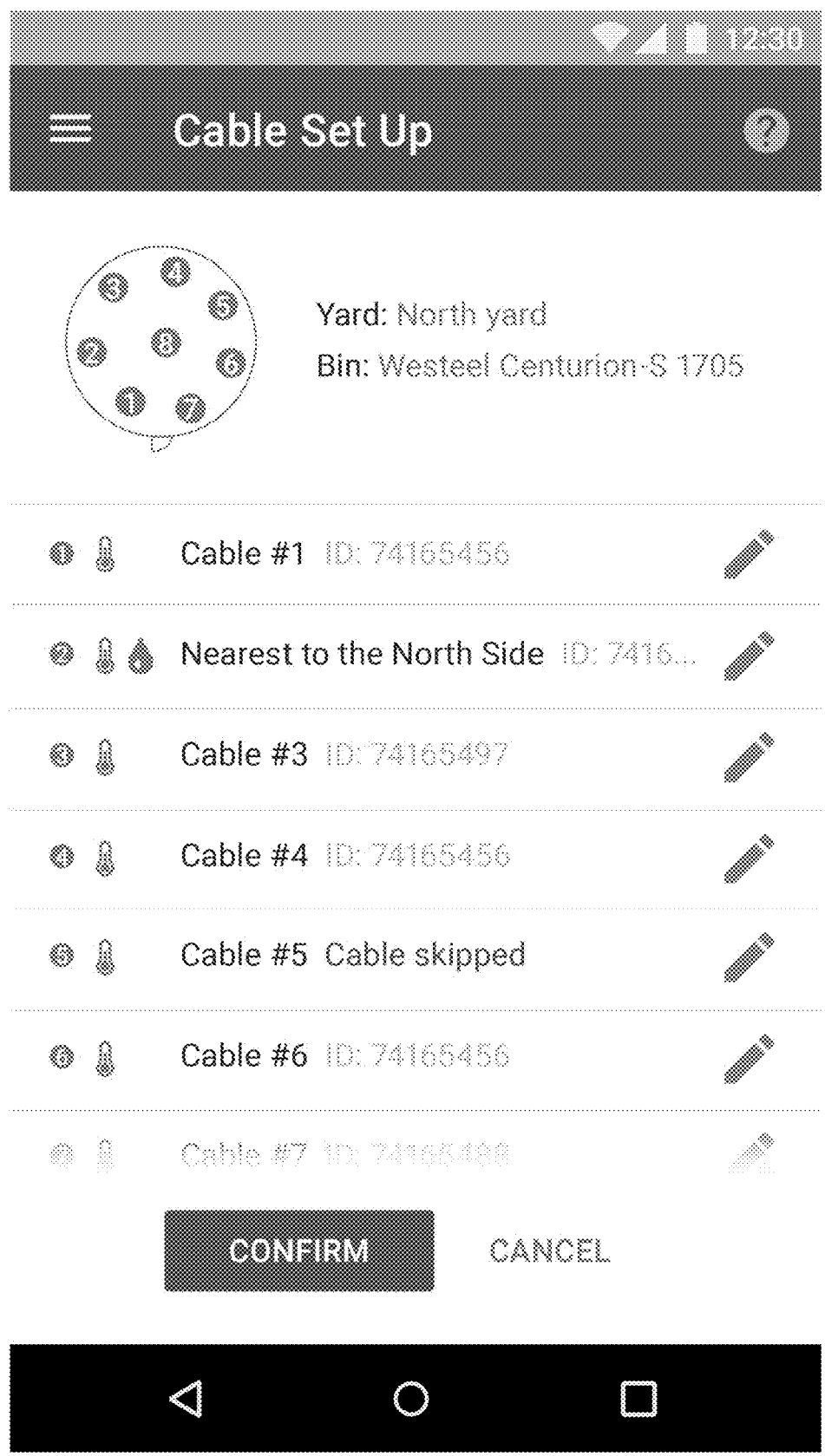
FIG. 20 depicts a graphical user interface displayed on a mobile device as part of the method of FIG. 15.
Figure 21:
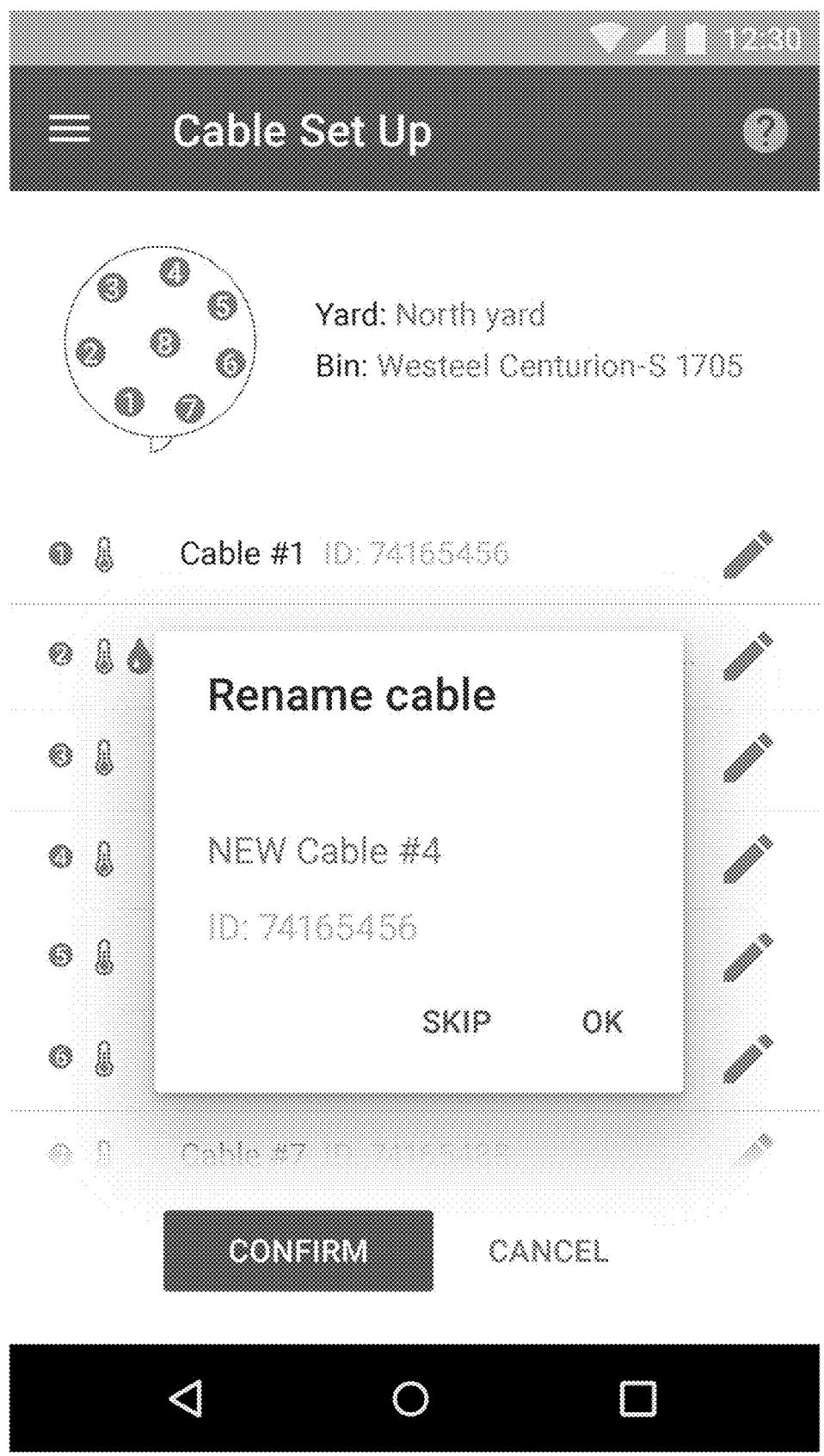
FIG. 21 depicts a graphical user interface displayed on a mobile device as part of the method of FIG. 15.
Figure 22:
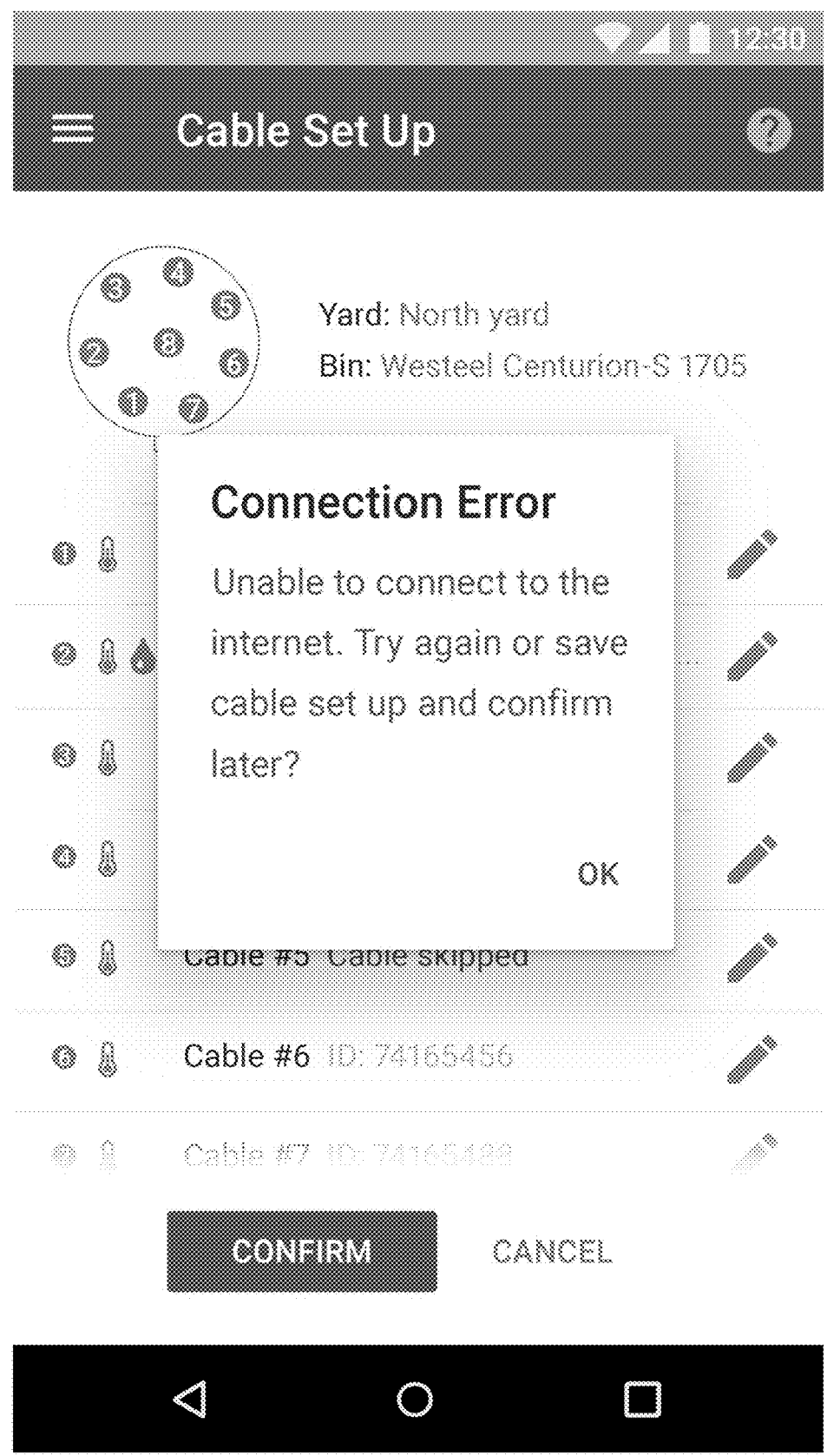
FIG. 22 depicts a graphical user interface displayed on a mobile device as part of the method of FIG. 15.
Figure 23:
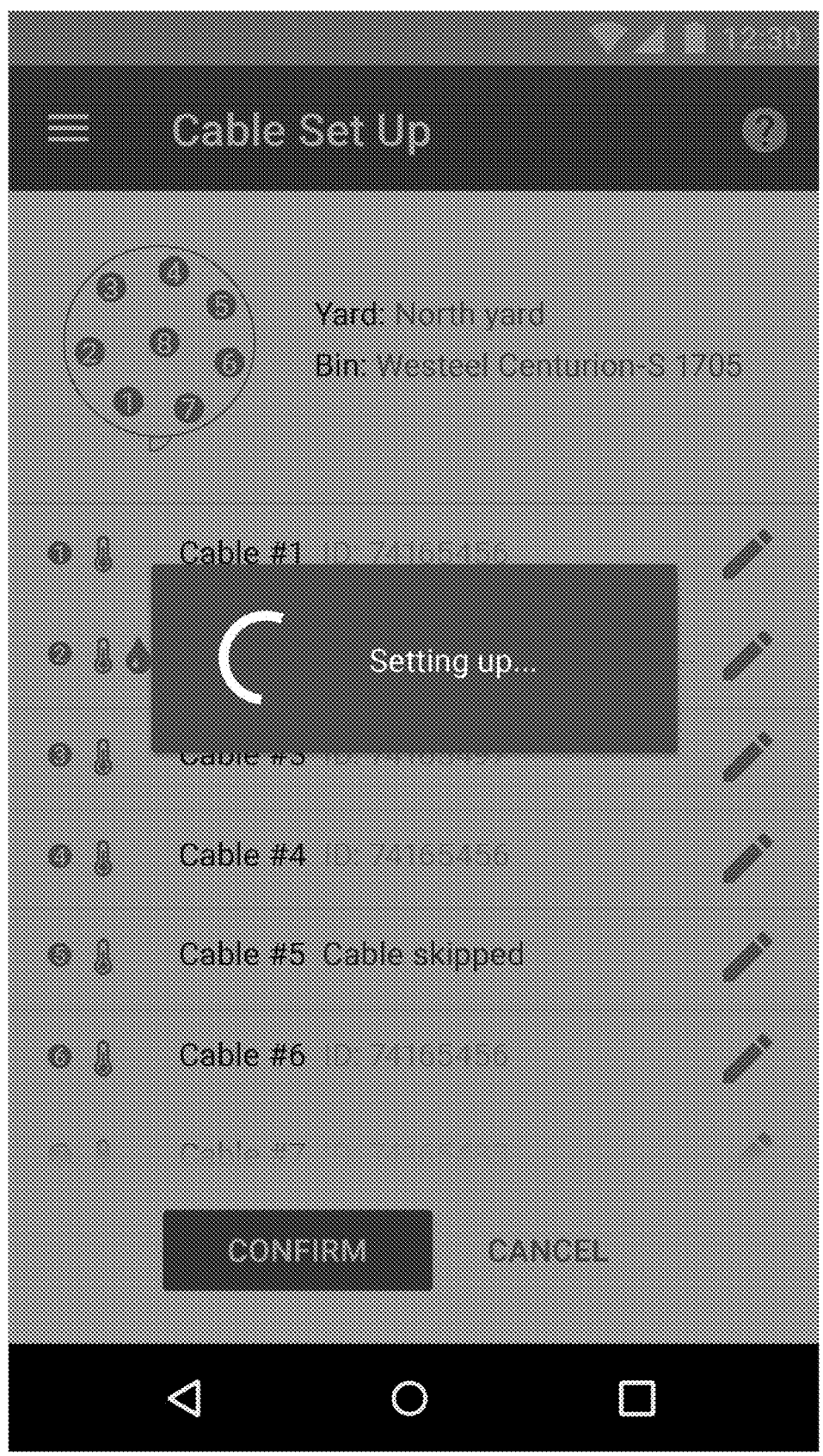
FIG. 23 depicts a graphical user interface displayed on a mobile device as part of the method of FIG. 15.
Figure 24:
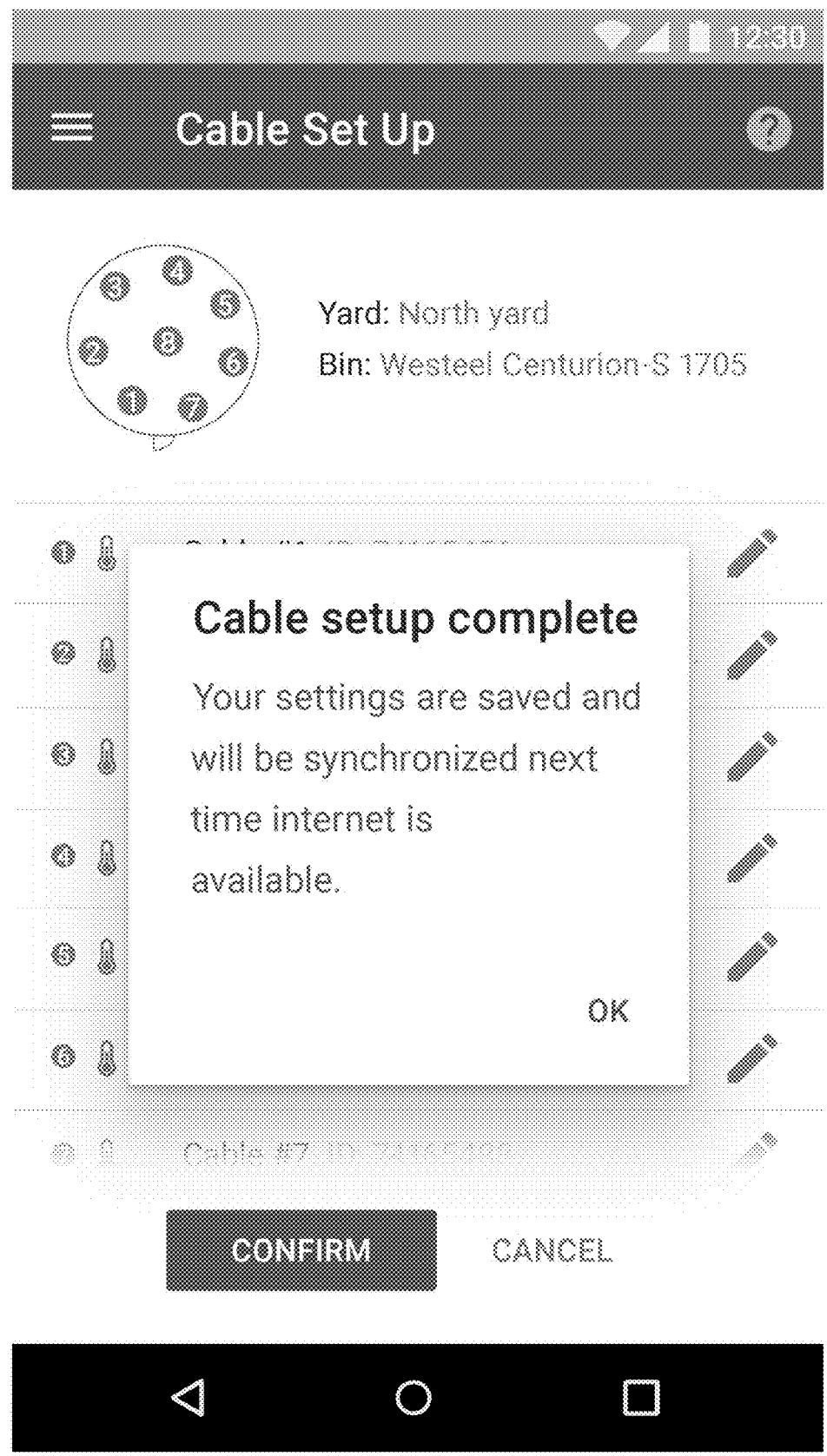
FIG. 24 depicts a graphical user interface displayed on a mobile device as part of the method of FIG. 15.
Figure 25:
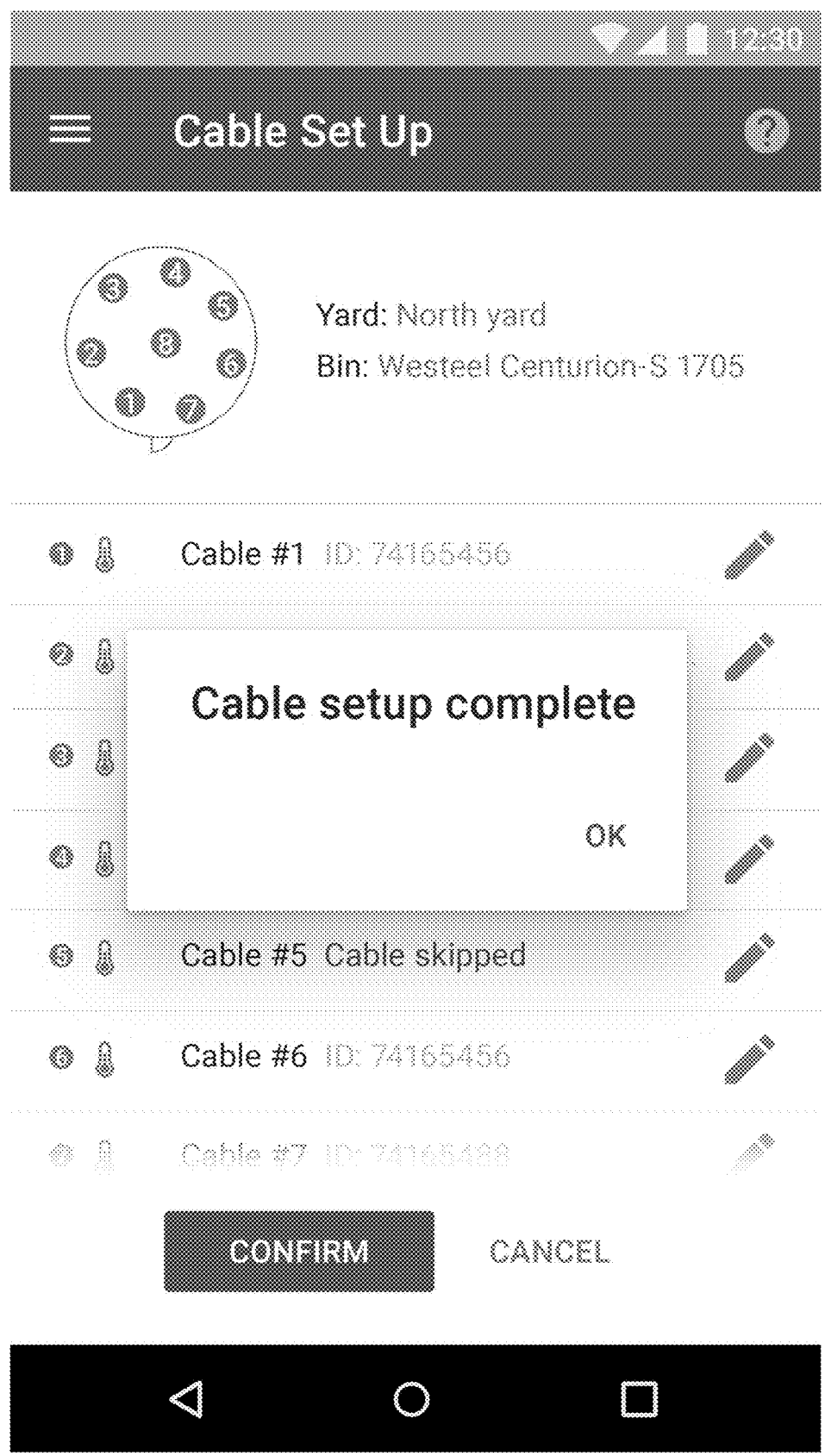
FIG. 25 depicts a graphical user interface displayed on a mobile device as part of the method of FIG. 15.

The method 200 of performing an automatic cable setup is summarized in the flowchart of FIG. 15. In a first step 210 of the method 200, the mobile device displays an initial setup screen, e.g. the user interface of FIG. 16 which may display the yard name and bin name. The app on the mobile device may then tell the user which cable to scan next. The app may also provide a screen to enable the user to skip to the next cable. FIG. 16 shows by way of example an onscreen alignment frame for reading a code, e.g. scanning a QR code at the base of the cable. FIG. 16 also provides options to skip the cable or cancel setup, as examples of other user interface elements that may be included. In step 220, the mobile device requests that the user scan the QR code or bar code affixed to the end of the sensor cable as shown by way of example in FIG. 17. At step 230, the mobile device requests that the user name the cable or to use default labels, e.g. using the UI depicted in FIG. 18. At step 240, the mobile device presents the user with an option to cancel, e.g. using the UI of FIG. 19. This may cause the app to exit or restart. At step 250, the mobile device displays cable identification information (e.g. names assigned to the various cables), e.g. using the UI of FIG. 20. At step 260, the mobile device provides an option to rename a cable using, e.g., the UI depicted in FIG. 21. At step 270, the mobile device displays a notification or message that the setup is progressing (i.e. that the device is processing the setup configuration) using e.g. the UI of FIG. 23. If no internet connection is available, a connection error message is displayed at step 280 using a user interface such as the one shown in FIG. 22. The data is stored i.e. buffered until it can be later transmitted when the internet connection is available again. The mobile device may present a message that the data will be later synchronized (step 290) by displaying a message such as the one shown by way of example in FIG. 24. If an internet connection is available, the data is transmitted/synchronized and the mobile device presents an indication that the cable setup is now complete (step 300) by presenting for example a user interface such as the one shown in FIG. 25. Although QR codes are described in this paragraph, it will be appreciated that non-optical codes may be used.

Figure 26A:
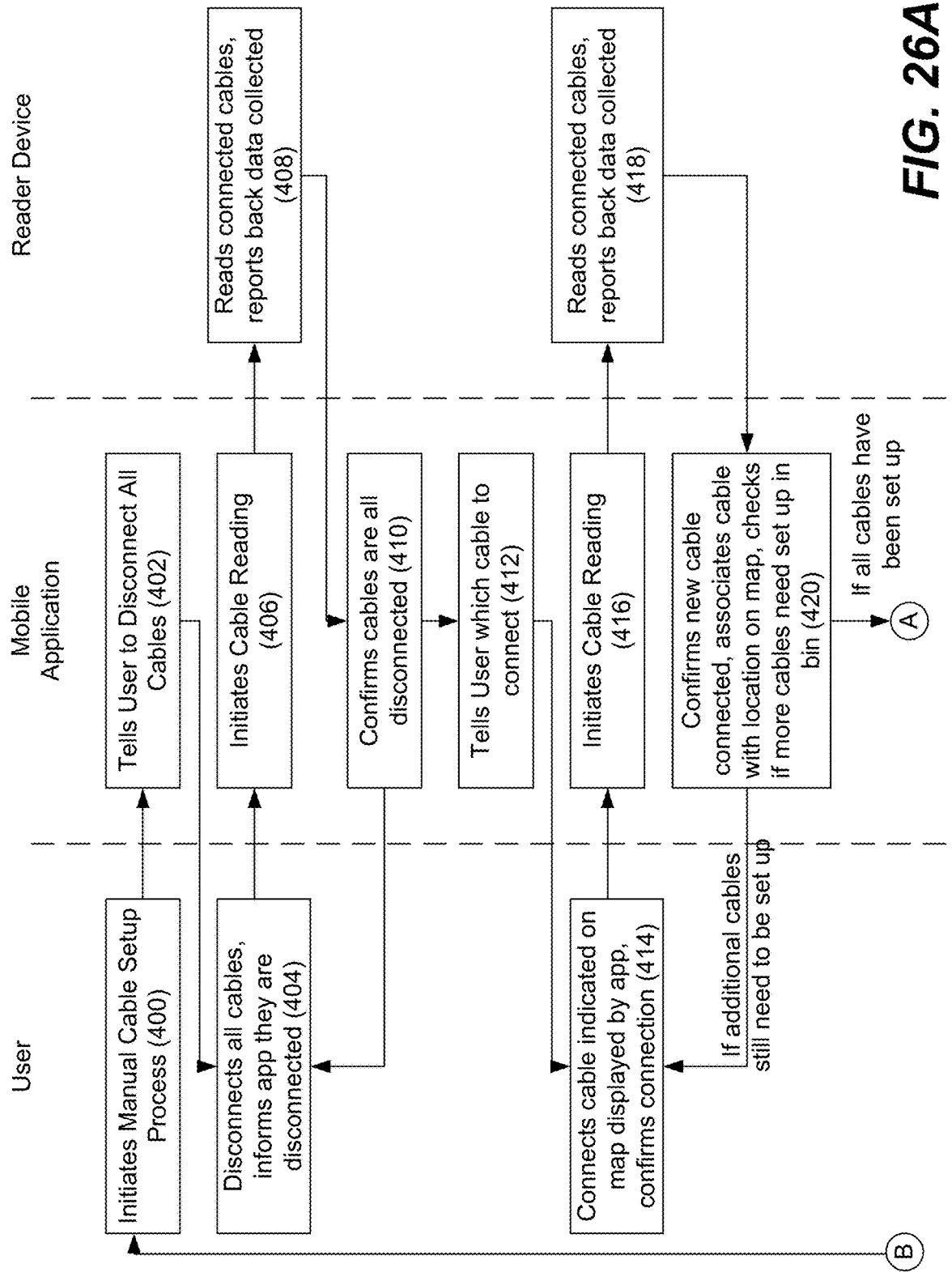
FIGS. 26A-26B depict an improved method for manual cable setup.
Figure 26B:
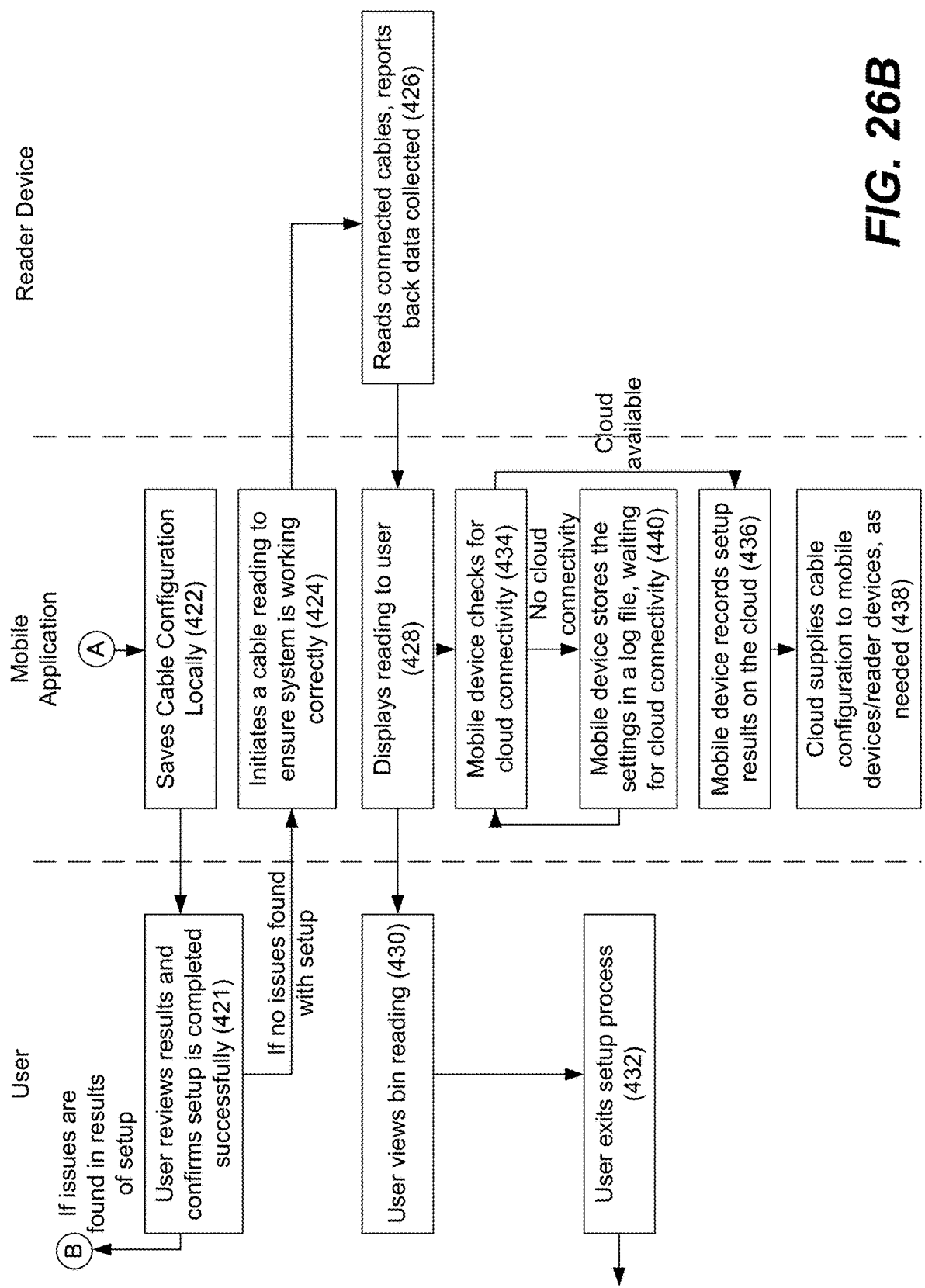

FIGS. 26A-26B depict an improved method for manual cable setup. As depicted in FIGS. 26A-26B, the user initiates the manual cable setup process (step 400), the mobile application tells the user to disconnect all cables (402). The user disconnects all cables and informs the app that they are disconnected (404). The mobile application initiates the cable reading (406). The reader device reads all connected cables and reports back the data collected (408). The mobile application confirms that the cables are all disconnected (410). If not all cables are disconnected, the method cycles back to tell the user to disconnect any of the cables that are still connected (404). The mobile application tells the user which cable to connect (412). The user connects the cable indicated on the map displayed by the mobile app, and confirms that it is connected (414). The mobile app initiates cable reading (416). The reader device reads connected cables and reports back the data collected (418). The mobile app confirms new cable has been connected and associates the cable with a location on the map, and checks if more cables need set up in the bin (420). If additional cables still need to be set up, the method returns to prompt the user to connect more cables. If all cables have been set up, the method proceeds to save the cable configuration locally (422). The user reviews the results and confirms setup is completed successfully (421). If issues are found in results of setup, the method cycles back to the beginning to re-initiate the cable setup process. If no issues are found, the mobile app initiates a cable reading to ensure system is working correctly (424). The reader device reads connected cables and report back data collected (426). The mobile app displays reading(s) to user (428). The user views bin reading (s) (430). The user can then exit the setup process (432). As shown in FIG. 26B, the mobile device checks for cloud connectivity (434). If the cloud is available, the mobile device records setup results on the cloud (436). The cloud then supplies cable configuration to mobile devices or reader devices as needed (438). If there is no cloud connectivity, the mobile device stores the settings in a log file, waiting for cloud connectivity (440).

Figure 27A:
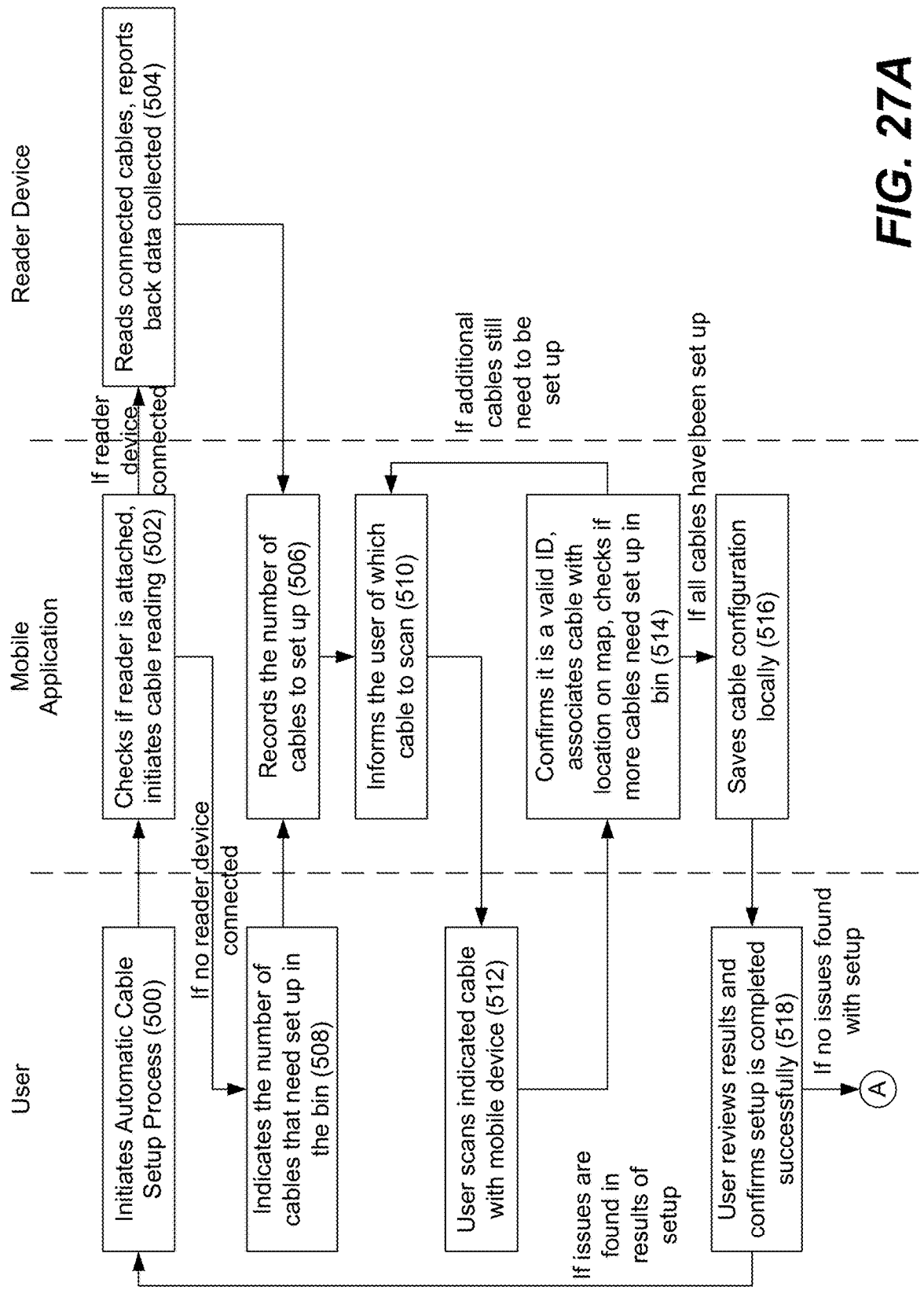
FIGS. 27A-27B depict an improved method for automatic cable setup.
Figure 27B:
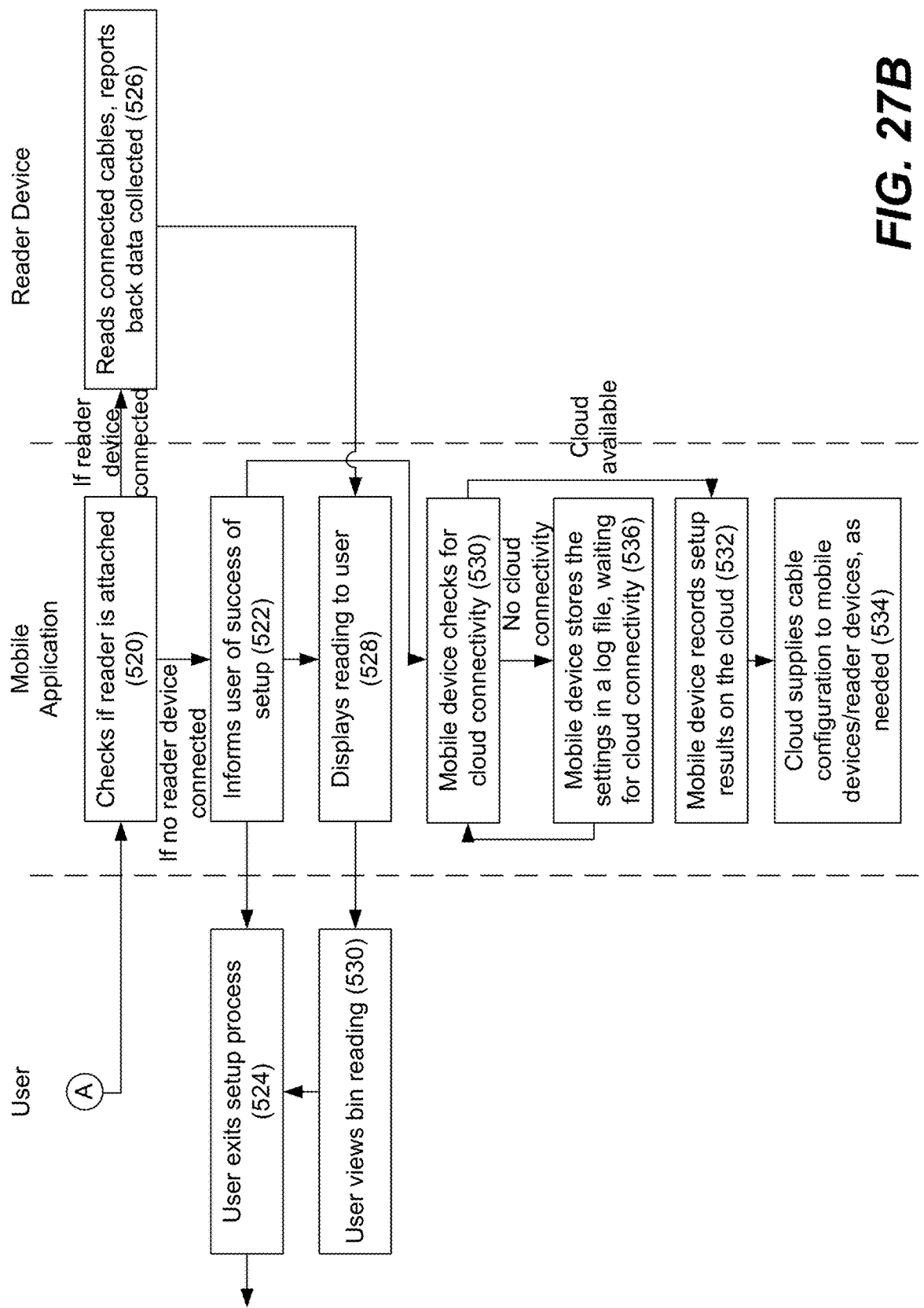

FIGS. 27A-27B depict an improved method for automatic cable setup. The user initiates the automatic cable setup process (step 500). The mobile application checks if a reader device is attached (or operational) and initiates cable reading (502). If the reader device is attached/operational, the reader device reads connected cables and reports back data collected (504). The mobile application then records the number of cables to set up (506). If no reader device is connected or operational, the user indicates the number of cables that need setup in the bin (508). The mobile application records the number of cables to set up (506). The mobile app informs the user of which cable to scan (510). The user scans the indicated cable with the mobile device (512). The mobile application confirms the scanned code is a valid ID, associates the cable with a location on a map, and checks if more cables need setup in the bin (514). If all cables have been set up, the mobile application saves the cable configuration locally (516). The user reviews the results and confirms setup is completed successfully (518). If there are issues found in the results of the setup, the method returns to the beginning to re-initiate the automatic cable setup process. If no issues are found with the setup, the method proceed with the mobile application checking if the reader device is attached or operational (520). If no reader device is connected, the mobile application informs the user that setup has been completed successfully (522). The user then exits the setup process (524). If the reader device is connected, the reader device reads connected cables and reports back data collected (526). The mobile application displays the reading (s) to the user (528). The user views the bin reading(s) (530) and then exits from the setup process (524). As shown in FIG. 27B, the mobile device checks for cloud connectivity (530). If the cloud is available, the mobile device records setup results on the cloud (532). The cloud then supplies cable configuration to mobile devices or reader devices as needed (534). If there is no cloud connectivity, the mobile device stores the settings in a log file, waiting for cloud connectivity (536).

The method or methods disclosed herein may be implemented in hardware, software, firmware or any combination thereof. Where implemented as software, the method steps, acts or operations may be programmed or coded as computer-readable instructions and recorded electronically, magnetically or optically on a fixed, permanent, non-volatile or non-transitory computer-readable medium, computer-readable memory, machine-readable memory or computer program product. In other words, the computer-readable memory or computer-readable medium comprises instructions in code which when loaded into a memory and executed on a processor of a computing device cause the computing device to perform one or more of the foregoing method(s).

A computer-readable medium can be any means that contain, store, communicate, propagate or transport the program for use by or in connection with the instruction execution system, apparatus or device. The computer-readable medium may be electronic, magnetic, optical, electromagnetic, infrared or any semiconductor system or device. For example, computer executable code to perform the methods disclosed herein may be tangibly recorded on a computer-readable medium including, but not limited to, a floppy-disk, a CD-ROM, a DVD, RAM, ROM, EPROM, Flash Memory or any suitable memory card, etc. The method may also be implemented in hardware. A hardware implementation might employ discrete logic circuits having logic gates for implementing logic functions on data signals, an application-specific integrated circuit (ASIC) having appropriate combinational logic gates, a programmable gate array (PGA), a field programmable gate array (FPGA), etc.

This method, system and computer-readable medium has been described in terms of specific embodiments, implementations and configurations which are intended to be exemplary only. Persons of ordinary skill in the art will appreciate, having read this disclosure, that many obvious variations, modifications and refinements may be made to the method, system and computer-readable medium.

It is to be understood that the singular forms "a", "an" and "the" include plural referents unless the context clearly dictates otherwise. Thus, for example, reference to "a device" includes reference to one or more of such devices, i.e. that there is at least one device. The terms "comprising", "having", "including", "entailing" and "containing", or verb tense variants thereof, are to be construed as open-ended terms (i.e., meaning "including, but not limited to,") unless otherwise noted. All methods described herein can be performed in any suitable order unless otherwise indicated herein or otherwise clearly contradicted by context. The use of examples or exemplary language (e.g. "such as") is intended merely to better illustrate or describe embodiments of the invention and is not intended to limit the scope of the invention unless otherwise claimed.

While several embodiments have been provided in the present disclosure, it should be understood that the disclosed systems and methods might be embodied in many other specific forms without departing from the scope of the present disclosure. The present examples are to be considered as illustrative and not restrictive, and the intention is not to be limited to the details given herein. For example, the various elements or components may be combined or integrated in another system or certain features may be omitted, or not implemented.

In addition, techniques, systems, subsystems, and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component whether electrically, mechanically, or otherwise. Other examples of changes, substitutions, and alterations are ascertainable by one skilled in the art and could be made without departing from the inventive concept(s) disclosed herein.

The invention claimed is:

1. A method of manually configuring sensor cables for measuring temperature and or moisture inside a grain bin, the method comprising:
   displaying on a display of a mobile device a representation of a cable configuration;
   displaying a request to the user to sequentially connect the sensor cables in locations sequentially indicated on the cable configuration; and
   assigning, using a processor of the mobile device, cable locations within the grain bin to each of the sensor cables in response to user input confirming that the sensor cables have been connected.

2. The method of claim 1 further comprising transmitting cable sensor configuration data representing the cable locations using a wireless transmitter of the mobile device.

3. The method of claim 1 further comprising displaying a user interface to name each of the sensor cables.

4. A computer-readable medium comprising programmed instructions which when stored by a memory of a mobile device and executed by a processor of the mobile device cause the mobile device to: display on a display of a mobile device a representation of a cable configuration; display a request to the user to sequentially connect the sensor cables in locations sequentially indicated on the cable configuration; and assign, using a processor of the mobile device, cable locations within a grain bin to each of the sensor cables in response to user input confirming that the sensor cables have been connected.

5. The computer-readable medium of claim 4 further comprising instructions to cause the mobile device to transmit cable sensor configuration data representing the cable locations using a wireless transmitter of the mobile device.

6. The computer-readable medium of claim 5 further comprising instructions to cause the mobile device to display a user interface to name each of the sensor cables.

7. A system for storing and monitoring grain, the system comprising:
- a grain bin for storing grain; and
- a plurality of sensor cables suspended within the grain bin, the sensor cables comprising sensors for sensing one or both of the temperature and humidity of the grain;
- a mobile device configured to:
  - display on a display of the mobile device a representation of a cable configuration;
  - display a request to the user to sequentially connect the sensor cables in locations sequentially indicated on the cable configuration; and
  - assign, using a processor of the mobile device, cable locations within the grain bin to each of the sensor cables in response to user input confirming that the sensor cables have been connected.

8. The system of claim 7 wherein the mobile device comprises a wireless transmitter to transmit sensor configuration data representing the cable locations.

9. The system of claim 7 wherein the mobile device is configured to display a user interface to name each of the sensor cables.

10. A method of manually configuring sensor cables for measuring temperature or moisture inside a grain bin, the method comprising:
- displaying on a display of a mobile device a representation of a cable configuration;
- displaying a request to the user to sequentially read codes on the sensor cables in locations sequentially indicated on the cable configuration;
- sequentially reading the codes on the sensor cables; and
- assigning, using a processor of the mobile device, cable locations within the grain bin to each of the sensor cables in response to user input confirming that the sensor cables have been read.

11. The method of claim 10 further comprising transmitting cable sensor configuration data representing the cable locations using a wireless transmitter of the mobile device.

12. The method of claim 10 further comprising displaying a user interface to name each of the sensor cables.

13. The method of claim 10, wherein the codes are optically scannable codes.

14. The method of claim 10, wherein the codes are RF codes.

15. A computer-readable medium comprising programmed instructions which when stored by a memory of a mobile device and executed by a processor of the mobile device cause the mobile device to: display on a display of the mobile device a representation of a cable configuration; display a request to the user to sequentially read codes on the sensor cables in locations sequentially indicated on the cable configuration; sequentially read the codes on the sensor cables; and assign, using a processor of the mobile device, cable locations within a grain bin to each of the sensor cables in response to user input confirming that the sensor cables have been read.

16. The computer-readable medium of claim 15 further comprising programmed instructions to cause the mobile device to transmit cable sensor configuration data representing the cable locations using a wireless transmitter of the mobile device.

17. The computer-readable medium of claim 15 further comprising programmed instructions to cause the mobile device to display a user interface to name each of the sensor cables.

18. The computer-readable medium of claim 15, wherein the codes are optically scannable codes.

19. The computer-readable medium of claim 15, wherein the codes are RF codes.

20. A system for storing and monitoring grain, the system comprising:
- a grain bin for storing grain; and
- a plurality of sensor cables suspended within the grain bin, the sensor cables comprising sensors for sensing one or both of the temperature and humidity of the grain;
- a mobile device configured to:
  - display on a display of the mobile device a representation of a cable configuration;
  - display a request to the user to sequentially read codes on the sensor cables in locations sequentially indicated on the cable configuration;
  - sequentially read the codes on the sensor cables; and
  - assign, using a processor of the mobile device, cable locations within the grain bin to each of the sensor cables in response to user input confirming that the sensor cables have been read.

21. The system of claim 20 wherein the mobile device is configured to display a user interface to name each of the sensor cables.

* * * * *

UNITED STATES PATENT AND TRADEMARK OFFICE
CERTIFICATE OF CORRECTION

PATENT NO. : 10,990,771 B2
APPLICATION NO. : 16/166793
DATED : April 27, 2021
INVENTOR(S) : Erron Leafloor and Craig Nimegeers Page 1 of 1

It is certified that error appears in the above-identified patent and that said Letters Patent is hereby corrected as shown below:

In the Claims

Column 10, Line 34, Claim 1, please delete the word "and".

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*